(12) United States Patent
Bau et al.

(10) Patent No.: US 8,697,007 B2
(45) Date of Patent: Apr. 15, 2014

(54) BIODETECTION CASSETTE WITH AUTOMATED ACTUATOR

(75) Inventors: Haim H. Bau, Swarthmore, PA (US); Changchun Liu, Philadelphia, PA (US); Xianbo Qiu, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 451 days.

(21) Appl. No.: 12/535,718

(22) Filed: Aug. 5, 2009

(65) Prior Publication Data

US 2010/0035349 A1 Feb. 11, 2010

Related U.S. Application Data

(60) Provisional application No. 61/086,573, filed on Aug. 6, 2008.

(51) Int. Cl.
*B01L 3/00* (2006.01)
*G01N 33/00* (2006.01)
*G01N 33/50* (2006.01)

(52) U.S. Cl.
USPC .......................................... 422/502; 422/68.1

(58) Field of Classification Search
None
See application file for complete search history.

(56) References Cited

U.S. PATENT DOCUMENTS

| | | |
|---|---|---|
| 5,098,660 A | 3/1992 | Devaney, Jr. |
| 5,229,297 A | 7/1993 | Schnipelsky et al. |
| 5,422,271 A | 6/1995 | Chen et al. |
| 5,568,912 A | 10/1996 | Minami et al. |
| 5,575,632 A | 11/1996 | Morris et al. |
| 5,593,804 A | 1/1997 | Chemelli et al. |
| 5,811,296 A | 9/1998 | Chemelli et al. |
| 6,180,062 B1 | 1/2001 | Naka et al. |
| 6,300,138 B1 | 10/2001 | Gleason et al. |
| 6,645,758 B1 | 11/2003 | Schnipelsky et al. |
| 6,942,836 B2 | 9/2005 | Freudenthal et al. |
| 2001/0052460 A1 | 12/2001 | Chien et al. |
| 2003/0152994 A1 | 8/2003 | Woudenberg et al. |
| 2005/0054113 A1 | 3/2005 | Bedingham et al. |
| 2005/0123454 A1 | 6/2005 | Cox |
| 2007/0041878 A1* | 2/2007 | Bryning et al. ............... 422/103 |
| 2007/0065346 A1* | 3/2007 | Henry et al. .................. 422/100 |
| 2007/0243627 A1* | 10/2007 | Takayama et al. ............ 436/180 |
| 2009/0186357 A1 | 7/2009 | Mauk |
| 2009/0226911 A1 | 9/2009 | Mauk |

FOREIGN PATENT DOCUMENTS

WO    WO 2008076395 A2 *  6/2008

OTHER PUBLICATIONS

Wang, Jing et al. "A disposable microfluidic cassette for DNA amplification and detection." Lab on a Chip (2006) 6 46-53.*
Weibel, Douglas B. et al. "Torque actuated valves for microfluidics." Anal. Chem. (2005) 77 4726-4733.*
Corstjens et al., "Use of Up-Converting Phosphor Reporters in Lateral-Flor Assays to Detect Specific Nucleic Acid Sequences: A Rapid, Sensitive DNA Test to Identify Human Papillomavirus Type 16 Infection", Clinical Chemistry, 2001, 47, 10, 1885-1893.

(Continued)

*Primary Examiner* — Christopher A Hixson
(74) *Attorney, Agent, or Firm* — Baker & Hostetler LLP

(57) ABSTRACT

Provided are analysis cassettes that include removable sealing layers and deformable connector layers that place various channels, chambers, and reservoirs on the cassettes into fluid communication with one another. The cassettes are suitable for use in self-contained, immunoassay devices that may be operated in an automated fashion. Also disclosed are methods for analyzing samples by use of the disclosed cassettes.

19 Claims, 21 Drawing Sheets

(56) References Cited

OTHER PUBLICATIONS

Findlay et al., "Automated Closed-Vessel System for In Vitro Diagnostics Based on Polymerase Chain Reaction", Clinical Chemistry, 38, 9, 1927-1933.

Product Brochure on DISKHALER Mar. 2006, Retrieved From the Internet at URL http://www.relenza.com/hcp/relenza-diskhaler-deliver-system.html on Nov. 5, 2009.

U.S. Appl. No. 12/515,616—National Stage Entry of PCT/US07/25699 filed Dec. 14, 2007, by Zongyuan Chen et al.

* cited by examiner

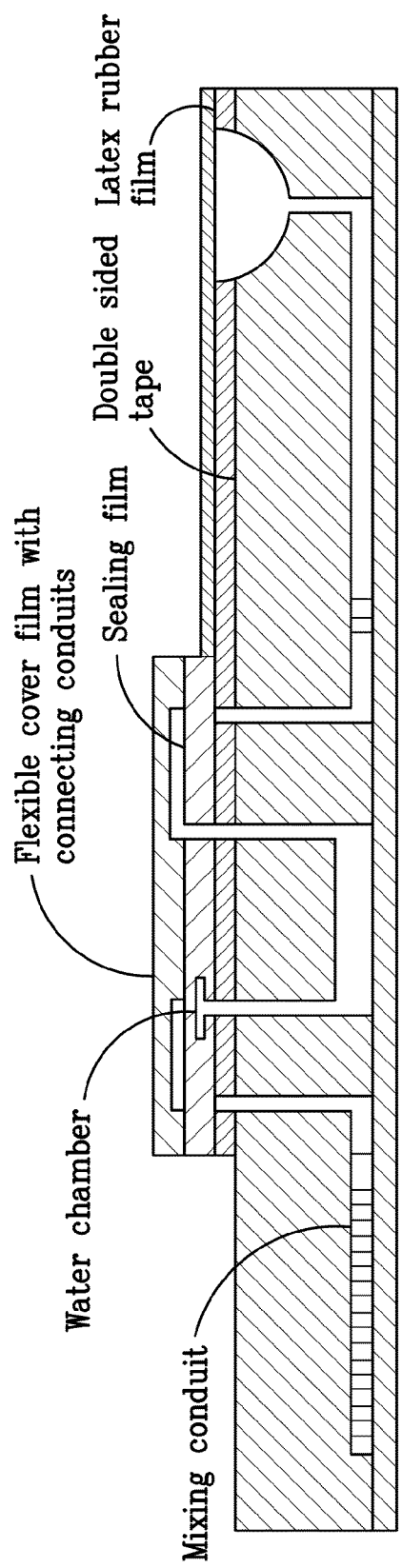
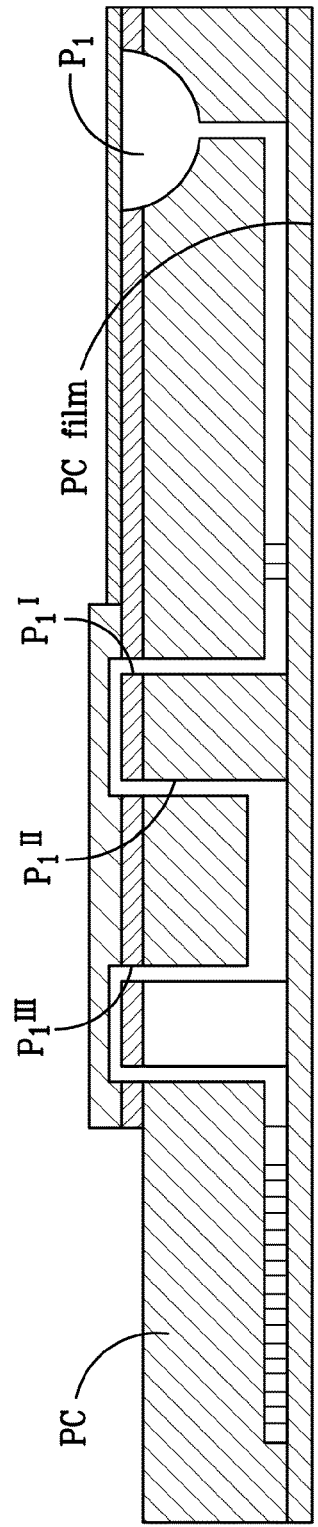
FIG. 1B  A-A
FIG. 1C  A-A

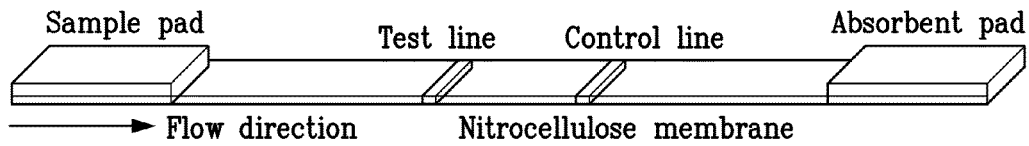
FIG. 8A
FIG. 8B
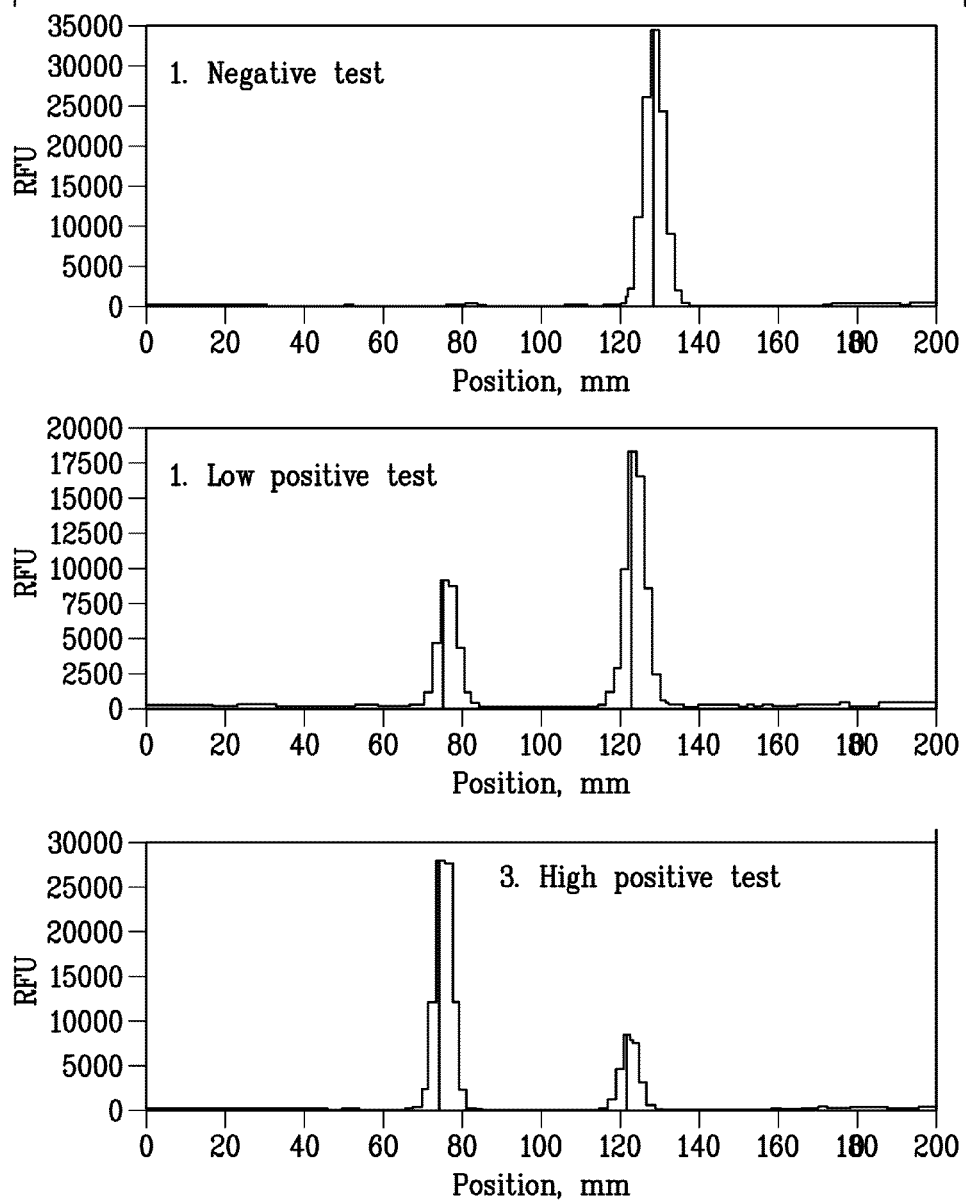

Mode: Single

1fg~20 copies

BIODETECTION CASSETTE WITH AUTOMATED ACTUATOR

CROSS-REFERENCE TO RELATED APPLICATIONS

This patent application claims the benefit of U.S. Provisional Patent Application Ser. No. 61/086,573, filed Aug. 6, 2008, the entirety of which application is incorporated by reference herein.

STATEMENT OF GOVERNMENT RIGHTS

This invention was made with U.S. Government support. The Government may have certain rights in the invention under National Institutes of Health grant number NIH/NIDCR UO1DE01785.

TECHNICAL FIELD

The present invention relates to the field of microfluidic devices.

BACKGROUND

The advancement of techniques and methods for detection of biological and non-biological samples for pathogens, drugs, toxins, and the like provides important tools for clinical practitioners as well as for military and paramedic personnel. Such techniques and methods for pathogen detection have additional application to fields other than medicine, including testing food, beverages, and consumer goods for pathogens or contaminants.

Detection techniques typically involve subjecting a sample to a prescribed sequence of fluid transfer, mixing, reaction, and detection steps, all within a contained fluidic system.

Certain of these devices are limited in application, however, because they may not be ideal for transport to and through a rugged field environment where pathogen testing may be necessary. Other devices are complex and are reliably operated only by trained personnel and may be slow to produce results. Accordingly, such systems are not well-suited for use by personnel lacking specialized training or by personnel who may be called upon to perform pathogen testing while under duress.

Further, existing detection systems arrange system components in a linear fashion wherein elements are only accessed sequentially, and may not be capable of effecting more intricate fluid actuation schemes, such as repeatedly transporting fluid between two or more components of a fluidic circuit before then transporting the fluid to subsequent downstream components. This limitation reduces the utility of existing systems in that intricate fluid transport schemes may be necessary to detect certain pathogens.

Accordingly, there is a need for robust devices capable of assaying samples for pathogens, drugs, toxins, bacteria, viruses, medical abnormalities, and the like. Because pathogen detection schemes include multiple mixing, washing, and reacting steps, there is a related need for an apparatus capable of actuating complex schemes of fluid motion. The value of such a device would be further enhanced if its use did not require a specially trained operator.

SUMMARY

In meeting the described challenges, the present invention first provides analysis cassettes comprising: a substrate, the substrate comprising a first conduit, the substrate comprising at least one reservoir, the at least one reservoir comprising at least one reservoir conduit, and the substrate comprising a second conduit; a removable sealing layer, the removable sealing layer at least partially sealing the first conduit, the at least one reservoir, and the second conduit; and a deformable connector layer, the deformable connector layer being capable of sealing at least a portion of the substrate, and the deformable connector layer being capable of placing the at least one reservoir in fluidic communication with at least the first conduit, with at least the second conduit, or both.

In a second aspect, the present invention provides analytic devices, comprising: a cassette having a fluidic element at least partially sealed with a deformable connecting layer; an actuator comprising an actuating plate capable of motion relative to the fluidic element, the plate comprising at least one projection, the actuator further comprising at least one moveable body contained within a housing, the moveable body positioned between the plate and the cassette such that motion of the at least one projection gives rise to the moveable body actuating the deformable sealing layer, the fluidic element, or both; and a device capable of controllably moving the actuating plate relative to the deformable sealing layer.

Also provided are methods of analyzing a sample, comprising: introducing a sample into an analysis cassette; the cassette comprising a substrate having at least a chamber and first and second channels, each channel being capable of fluidic communication with the environment exterior to the cassette, the cassette comprising a removable sealing layer, the removable sealing layer at least partially sealing at least one of the first channel, the second channel, or the chamber; and the cassette comprising a deformable connector layer, the deformable connector layer being capable of at least partially sealing at least one of the first channel, the second channel, or the chamber, and the deformable connector layer being capable of placing at least two of the first channel, the second channel, or the chamber in fluid communication with one another; displacing at least a portion of the removable sealing layer; replacing the displaced portion of the removable sealing layer with the connector layer to as to place the at least one chamber in fluidic communication with at least the first conduit, with at least the second conduit, or both; and processing the sample by actuation of at least a portion of the deformable connector layer, the processing being accomplished by the movement of an actuator relative to the deformable connector layer, the actuator comprising one or more physical features arranged so as to effect a predetermined schedule of processing steps when the actuator is moved relative to the deformable connector layer.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 8 illustrates results of an HIV test performed according to the present invention;

DETAILED DESCRIPTION OF ILLUSTRATIVE EMBODIMENTS

Figure 1A:
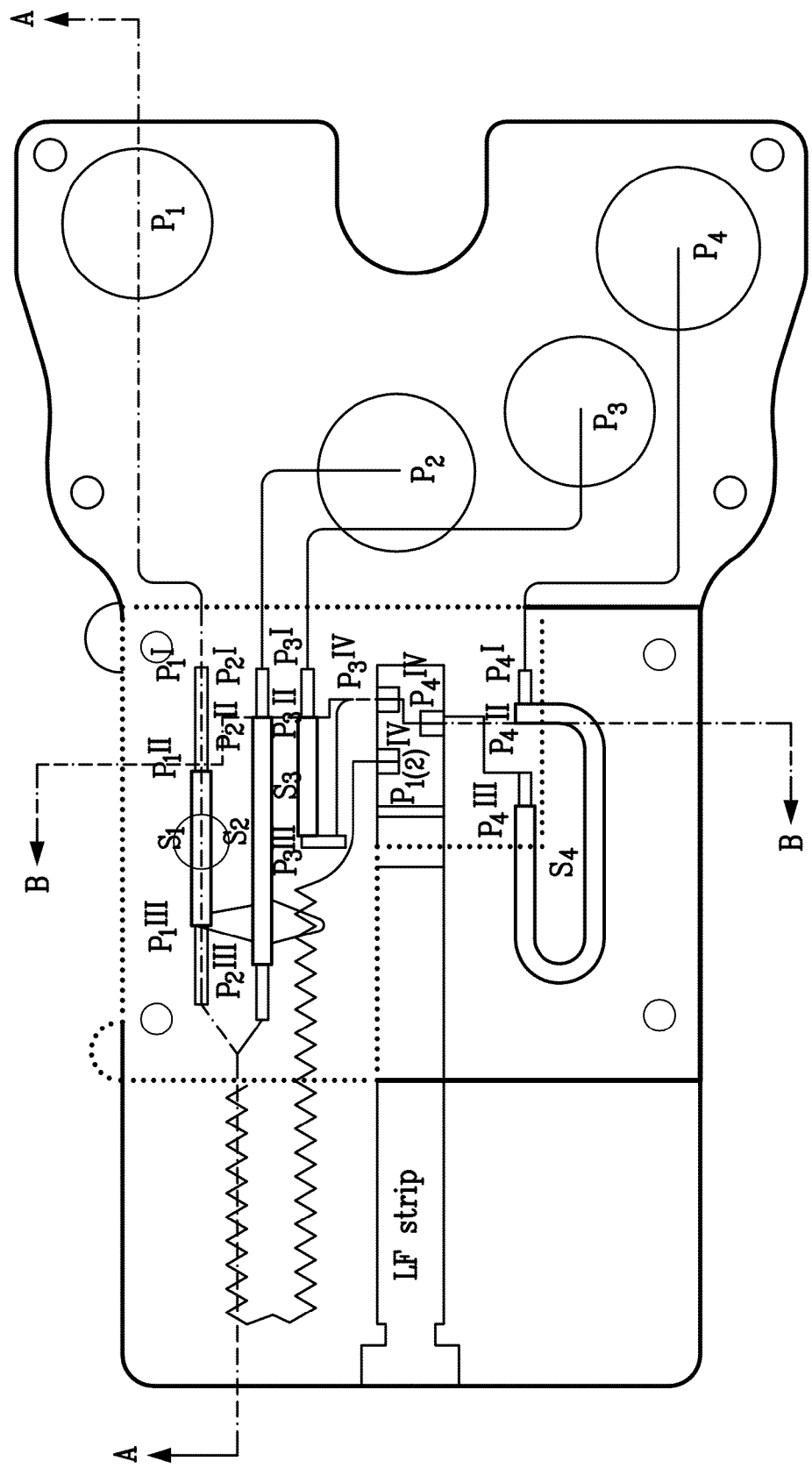
FIG. 1 illustrates a schematic view of a cassette according to the present invention.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first aspect, the present invention provides analysis cassettes. The disclosed cassettes include a substrate, with the substrate comprising a first conduit and at least one reservoir. The least one reservoir suitably includes at least one reservoir conduit. The substrate also suitably includes a second conduit.

The cassettes also suitably include a removable sealing layer that at least partially seals the first conduit, the at least one reservoir, and the second conduit—or any combination of these. The cassettes also suitably include a deformable connector layer that is capable of sealing at least a portion of the substrate, and is also suitable capable of placing the at least one reservoir in fluidic communication with at least the first conduit, with at least the second conduit, or both.

The substrates suitably include a polymer, a metal, a glass, a ceramic, or any combination thereof. Polycarbonate, polystyrene, polymethylmecarcylate, polyethylene, polypropylene, and the like are all considered especially suitable substrate materials. Other plastics may be used, and, in some embodiments, glasses or metals. The substrate may also include a coating. The substrates are from about 0.5 millimeters to 1 centimeter in thickness, although thicker and thinner substrates may be suitable, such as substrates of about 1 mm, about 5 mm, about 10 mm, about 50 mm, or even about 75 mm. The substrates are suitably between about 1 mm and about 0.5 cm in thickness, although the optimal thickness will be dictated by the needs of the user and can be easily determined without undue experimentation.

The first conduit suitably includes a cross-sectional dimension in the range of from about 0.01 micrometers to about 5000 micrometers. The conduit may also be between about 1 micrometers and 500 micrometers, or from about 10 micrometers to about 50 micrometers. The second conduit and reservoir conduit are also suitably between about 0.01 micrometers to about 5000 micrometers, or 1 micrometers and 500 micrometers, or from about 10 micrometers to about 50 micrometers. Any or all of these conduits may be of the same or of different sizes.

The reservoir suitably contains a fluid, although the reservoir may contain air or other gases as necessary. Suitable fluids include reagents, buffers, acids, bases, dyes, labels, and the like. Biological molecules, such as antibodies, antigens, proteins, and the like, may also be contained within a reservoir. The reservoir may be between about 0.1 nanoliters to about 10 milliliters, and is suitably between 0.01 milliliters and 1 milliliter. Reservoirs of 0.1 ml, 0.2 ml, and 0.5 ml are also suitable.

In suitable embodiments, at least one of the first conduit, the second conduit, or the reservoir conduit is capable of fluid communication with the environment exterior to the analysis cassette. This enables the cassette to vent to the external environment or, in some cases, to receive fluids, air, gases, or other inputs from the external environment.

The removable sealing layer of the cassettes may include a polymer, a metal, a glass, a ceramic, and the like. The material is suitably flexible or peelable, although rigid materials are useable. In some embodiments, the sealing layer includes an adhesive used to bond the layer to the substrate. In other embodiments, the substrate includes an adhesive. The sealing layer suitably includes a thickness of between about 1 micrometer to about 1000 micrometers, or between about 10 and about 100 micrometers, or even between about 20 and about 50 micrometers. At least a portion of the removable sealing layer is suitably affixed to at least a portion of the cassette. In some embodiments, the sealing layer is peeled back; in others, the layer is removed entirely from the cassette.

Figure 13:
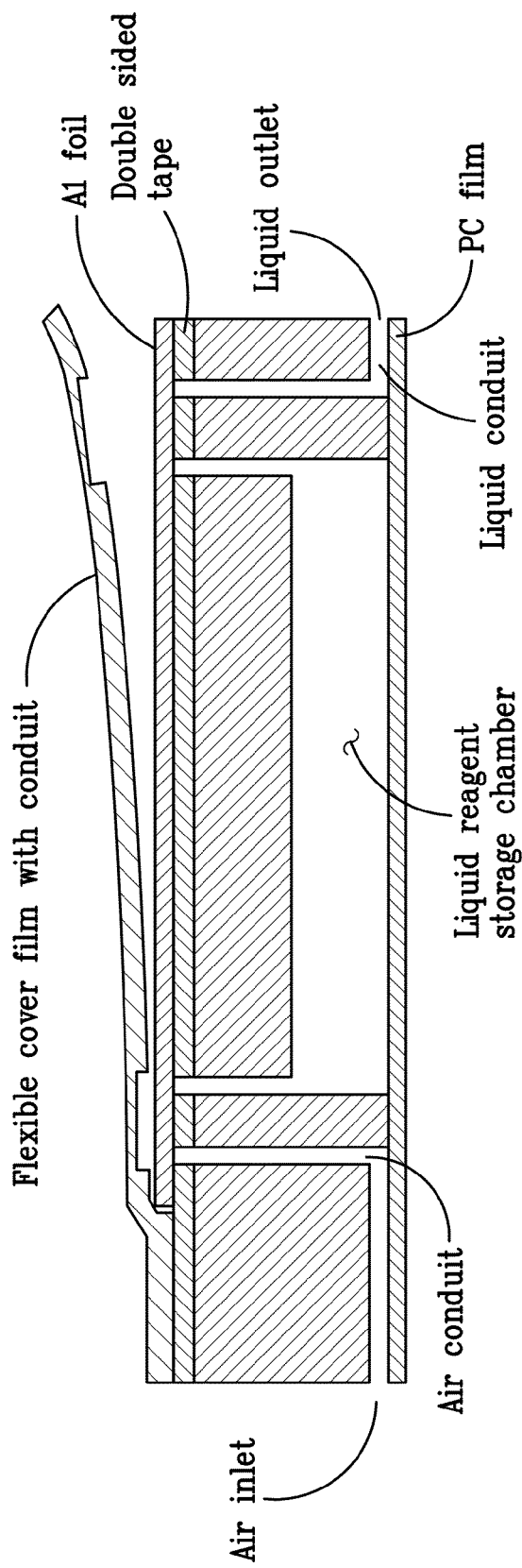
FIG. 13 illustrates a cross-sectional view of a device according to the present invention.

The deformable connector layer comprises at least one channel, as shown in, e.g., FIG. 13. In such embodiments, the connector layer is configured such that the at least one channel is capable of placing the at least one reservoir in fluidic communication with at least the first conduit, with at least the second conduit, or both. An exemplary, non-limiting example of this is shown in FIG. 13.

In some embodiments, at least a portion of the deformable connector layer is bonded to the substrate. This is shown in, e.g., FIG. 13. In such embodiments having at least a portion of the layer bonded to the substrate, the layer is effectively pre-aligned to the substrate such that when the layer is applied to the substate, any channels or other structures in the layer (e.g., a valve, an inlet, an outlet, and the like) are properly positioned above any fluidic elements, conduits, or other structures on the substrate to which they may be mated. In some embodiments, one or more portions of the deformable connector layer or the substrate (or both) include an adhesive in order that the connector layer is sealably applied to the cassette. Double-sided tape, as shown in FIG. 13 is also a suitable way to effect bonding or adhesion between the substrate and films or layers. In some embodiments, the tape or other sealing layer may be peeled away so as to allow the channels in the connector-capping layer to place various components or elements in fluid communication with one another. In this way, the tape or sealing layer can be used to prevent mixing (or, in some embodiments, other fluid communication) between elements until the user is ready to use the device. The sealing tape also, in some embodiments, serves the purpose of preventing evaporation of reagents or the entry of moisture into the device.

The cassettes of the present invention include, in suitable embodiments, detector modalities. Detector modalities include, non-exhaustively, lateral flow strips, microarrays, bead arrays, functionalized surfaces, or other materials or devices capable of specific binding or other detection of specific biological targets. Other detector modalities will be apparent to those of ordinary skill in the art.

Also provided are analytic devices. These devices include a cassette having a fluidic element at least partially sealed with a deformable connecting layer and an actuator comprising an actuating plate capable of motion relative to the fluidic element, the plate comprising at least one projection.

The actuators suitably include at least one moveable body contained within a housing, the moveable body positioned between the plate and the cassette such that motion of the at least one projection gives rise to the moveable body actuating the deformable sealing layer, the fluidic element, or both. The analytic devices also suitably include a device capable of controllably moving the actuating plate relative to the deformable sealing layer.

A fluidic elements suitable for the disclosed devices includes a chamber, a channel, a reservoir, a valve, a mixer, a vent, a splitter, a switch, a vent, and the like.

Reservoirs may contain a buffer, an acid, a base, a growth medium, a dye, a label, a reagent, a biological material, a suspension, air, a gas, and the like. Mixers may include one or more particular flow paths—including a zigzag path or a three-dimensional bend. Other mixers include pillars embedded in a conduit, or any other features that introduce secondary flows, vortices, and the like.

The disclosed analytic devices also suitably include a detector modality; suitable modalities are described elsewhere herein. The detector modality may be positioned on or within the cassette, but may also be positioned on or within the actuator. In some embodiments, the detector is external to the cassette, the actuator, or both.

The cassettes suitably include at least one vent to the exterior environment, and, in some embodiments, include at least one inlet port, at least one outlet port, or both. The inlets and outlets may be sealable or open to the external environment, and may include filters, screens, valves, and the like.

Cassettes suitably include two or more fluidic elements capable of fluid communication with one another. For example, the cassette might include a mixer or zig-zag path in fluidic connection with a reservoir or reactor chamber. Alternatively, the cassette may include a vent in fluid communication with a reservoir.

In suitable embodiments, the plate of the device is disc-shaped, although the plate need not be circular is shape. The plate suitably includes projections like bumps, pyramids, ramps, wedges, and the like. Ramps and wedges are considered particularly suitable because they can exert a controllable force on any element or layers to which they may come into contact. Wedges and ramps are also considered suitable because they may, depending on the configuration of the cassette, be useful in applying a force to a fluidic element and then lock into place. The projections may be solid or hollow, and are suitably positioned such that movement of the actuating plate effects depression of the deformable sealing layer, actuation of a fluidic element, or both, in a predetermined sequence.

Actuators according to the present invention are suitably capable of placing at least a portion of the body into physical contact with the deformable sealing layer. This contact is suitably under pressure.

The actuator suitably includes an opening capable of accepting at least a portion of the cassette. An example of this is shown in FIG. 3, which depicts an actuator capable of accommodating a cassette.

The moving devices are suitably capable, as shown in FIG. 4, of rotating the actuating plate. This suitably results in one or more projections on the actuating plate coming into contact with the deformable sealing layer so as to actuate one or more fluidic elements. The device may be capable of rotating the actuating plate at a constant rate or at a variable rate.

Figure 3:
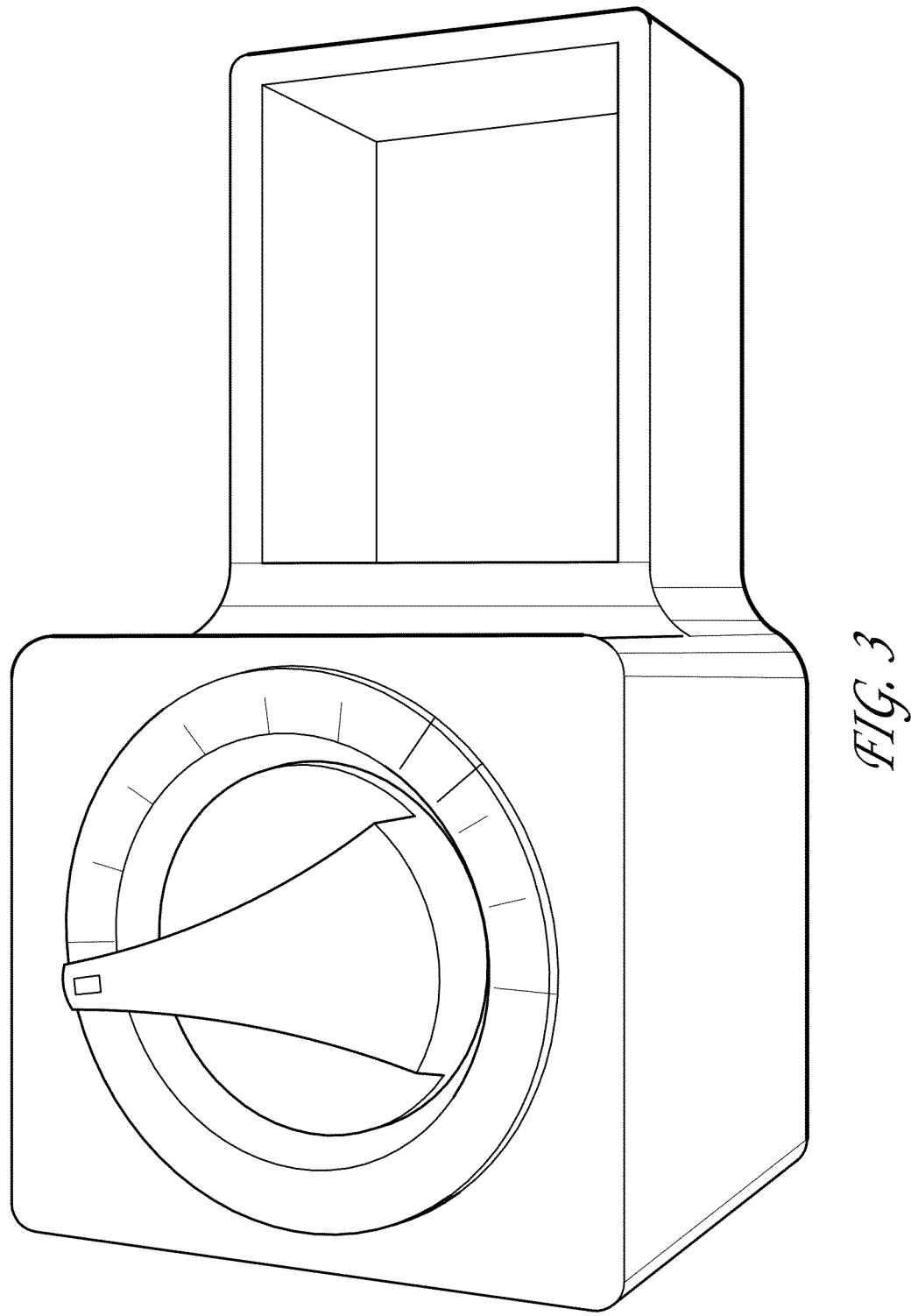
FIG. 3 illustrates an actuator and spring-wound timer according to the present invention.

The devices of the present invention also suitably include, as shown in FIGS. 3 and 4, a timer. The device may also include an energy storage device, such as a battery, a spring, a rubber band, and the like. As shown in FIG. 3, the analytic devices may include a spring-loaded timer, the movement of which rotates a projection-bearing plate so as to actuate a deformable connecting layer and an underlying fluidic element. The energy storage device may—as in the case of a wind-up time—be capable of being manually recharged. The moving device may also include a motor, and is suitably in mechanical connection with the actuating plate.

In some embodiments, the cassettes include a removable film sealing a fluidic element. The film may include a polymer, a rubber, a ceramic, a glass, a metal, or any combination thereof.

As described elsewhere herein, the cassettes' deformable connecting layer may place two or more fluidic elements in fluidic communication with one another. Suitable connecting layers materials are described elsewhere herein.

In some embodiments, the actuator, the device, or both, are integrated into the cassette. In other embodiments, the actuator and device are integrated together.

The body within the of the described analytic devices is suitably a sphere, as shown in FIG. 4. Bodies of other shapes—e.g. ovoid—are also suitable, depending on the needs of the user. The body is suitably contained within the housing such that the body's movement within the housing is essentially orthogonal to the deformable sealing layer, as shown in FIG. 4. In some embodiments, the analytic devices further include a spring located within the housing and being capable of contact with the body, which spring may exert pressure on the body so as to modulate the body's movement within the housing.

In some embodiments, the analytic devices include an actuator that accepts multiple cassettes at one time. In such embodiments, individual cassettes are addressed by a individual movement control devices. In other embodiments, a single, centralized movement control device addresses multiple cassettes.

Additionally provided are methods of analyzing a sample. These methods include introducing a sample into an analysis cassette; the cassette comprising a substrate having at least a chamber and first and second channels, each channel being capable of fluidic communication with the environment exterior to the cassette, the cassette comprising a removable sealing layer, the removable sealing layer at least partially sealing at least one of the first channel, the second channel, or the chamber; and the cassette comprising a deformable connector layer, the deformable connector layer being capable of at least partially sealing at least one of the first channel, the second channel, or the chamber, and the deformable connector layer being capable of placing at least two of the first channel, the second channel, or the chamber in fluid communication with one another; displacing at least a portion of the removable sealing layer; replacing the displaced portion of the removable sealing layer with the connector layer to as to place the at least one chamber in fluidic communication with at least the first conduit, with at least the second conduit, or both; and processing the sample by actuation of at least a portion of the deformable connector layer, the processing being accomplished by the movement of an actuator relative to the deformable connector layer, the actuator comprising one or more physical features arranged so as to effect a predetermined schedule of processing steps when the actuator is moved relative to the deformable connector layer Displacing the removable sealing layer is suitably accomplished by peeling. The sealing layer is useful in sealing the cassette against the external environment until use. Replacing the displaced portion of the removable sealing layer with the connector layer comprises pressing, adhering, clamping, and the like. This is shown in FIG. 1(b) and (c), which figure shows the displacement—i.e., removal—of the removable layer and the application of the connector layer in its place. This is normally accomplished manually, although these steps may be accomplished in an automated fashion.

The processing of the sample suitably includes transporting a fluid along at least a portion of a channel. Processing also suitably includes contacting the sample with one or more reagents and identifying the presence of one or more biological species in the sample. The identification of biological species is suitably accomplished by a detector modality, as described elsewhere herein.

In some suitable embodiments, the processing is at least partially controlled by a device that is itself capable of controllably moving the actuator relative to the deformable connector layer. Such devices include, for example, spring-loaded timers, as described elsewhere herein and as shown in FIGS. 3 and 4. In some embodiments, the device moves the actuator relative to the deformable connector layer by releasing stored energy—as in the operation of a spring-wound timer.

Figure 14:
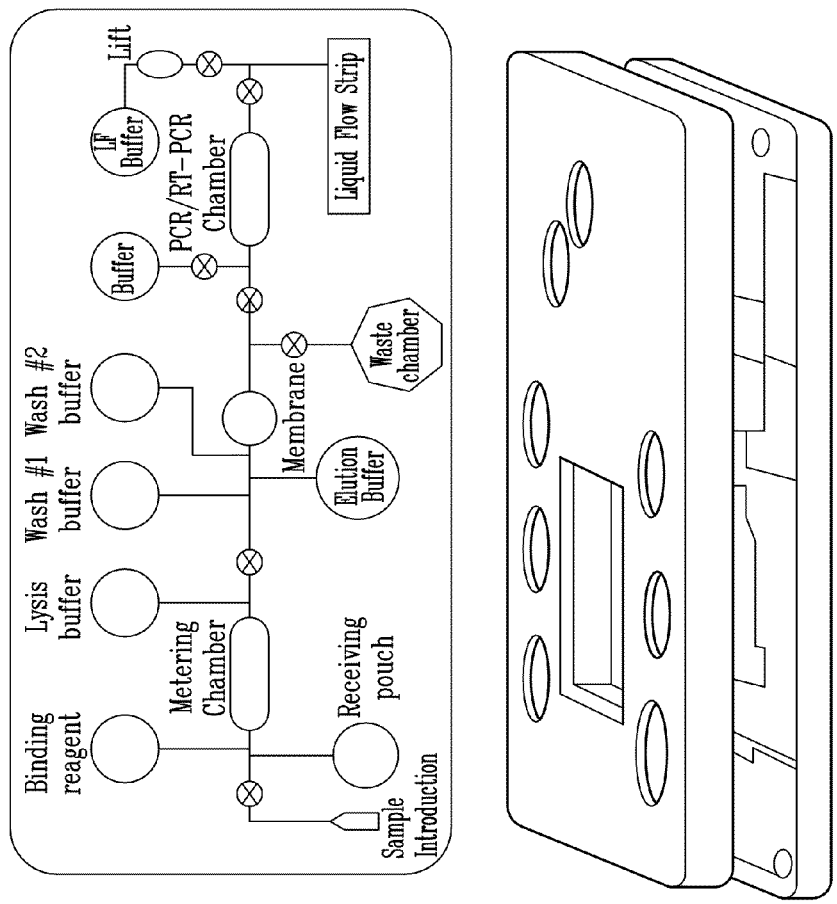
FIG. 14 illustrates a silica-membrane based nucleic acid cassette according to the present invention.
Figure 15A:
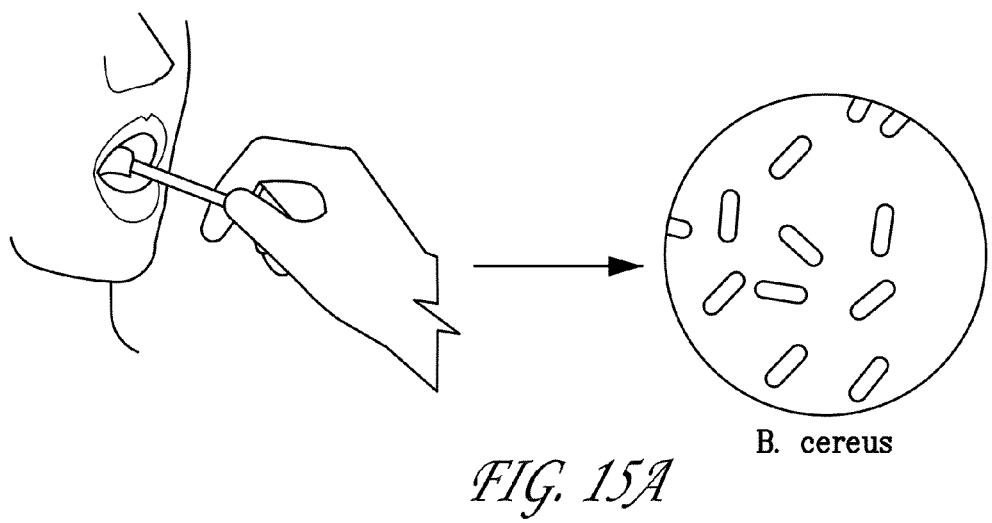
FIGS. 15A-F illustrate the use of the present invention in a PCR-based detection scheme.
Figure 15B:
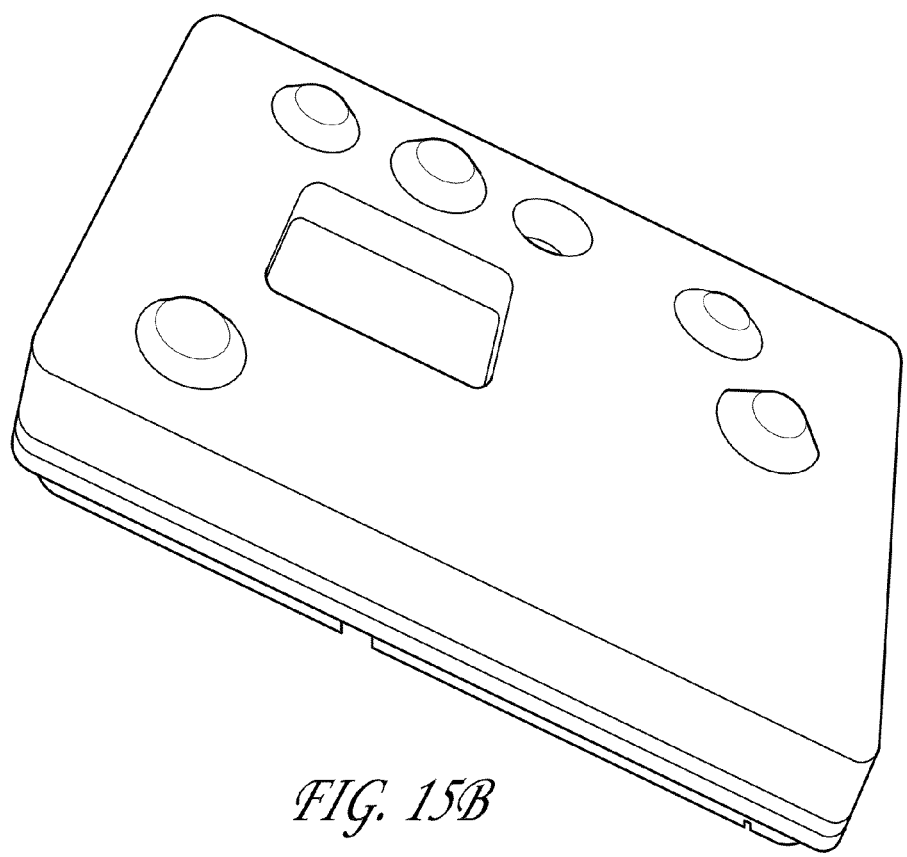
Figure 15C:
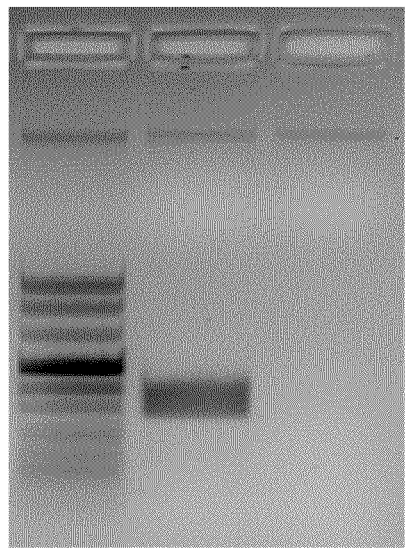
Figure 15D:
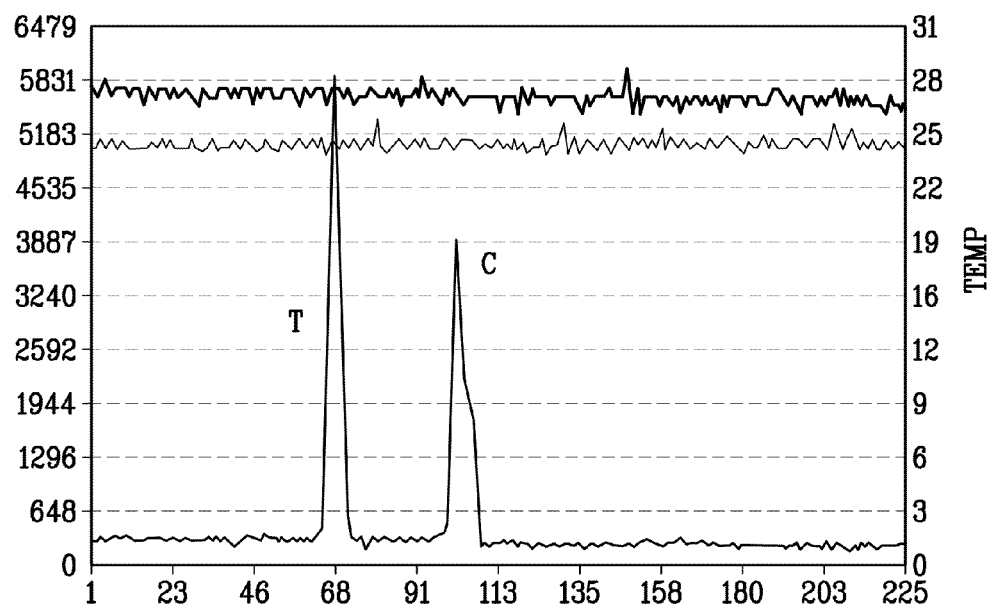
Figure 15E:
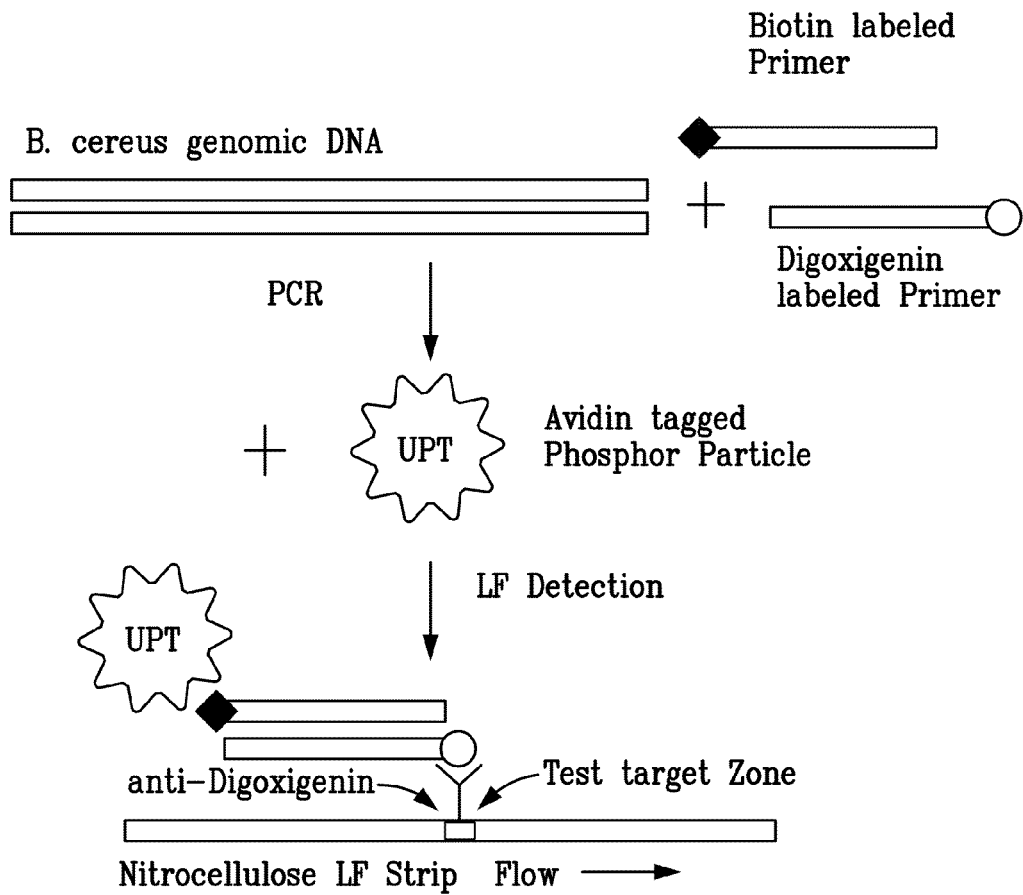
Figure 15F:
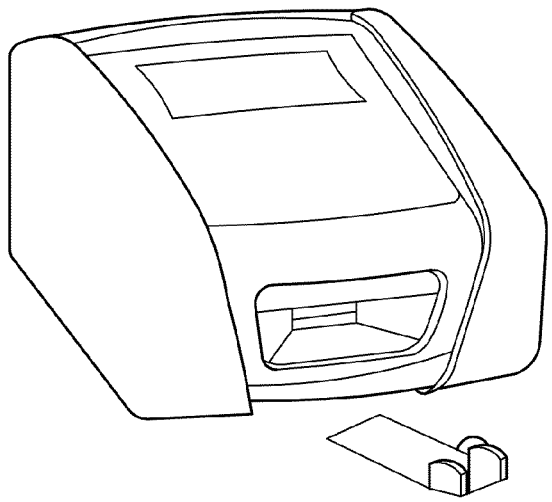
Figure 16A:
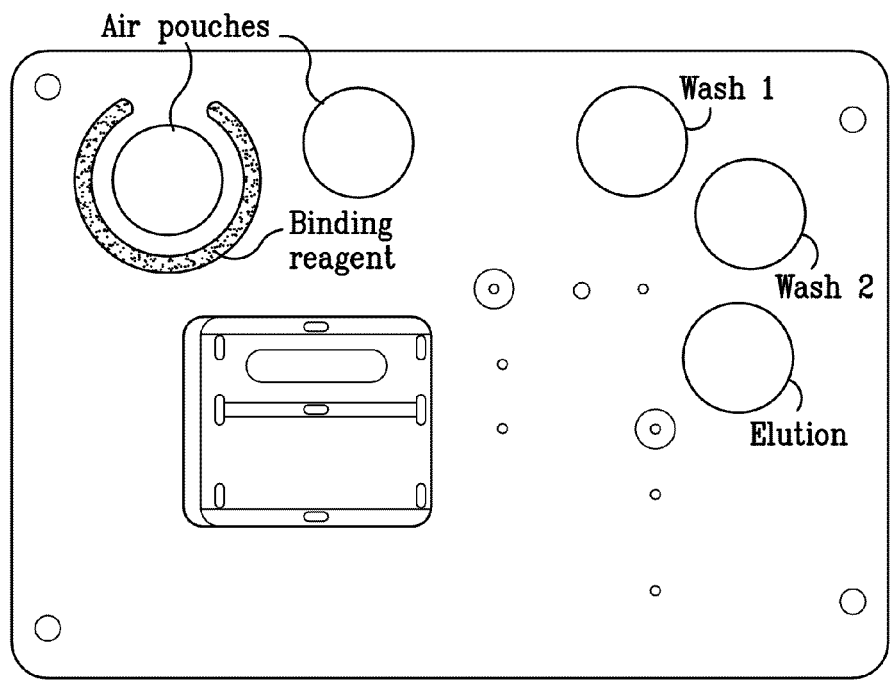
FIGS. 16A-D depict a nucleic-acid cassette and actuator.
Figure 16B:
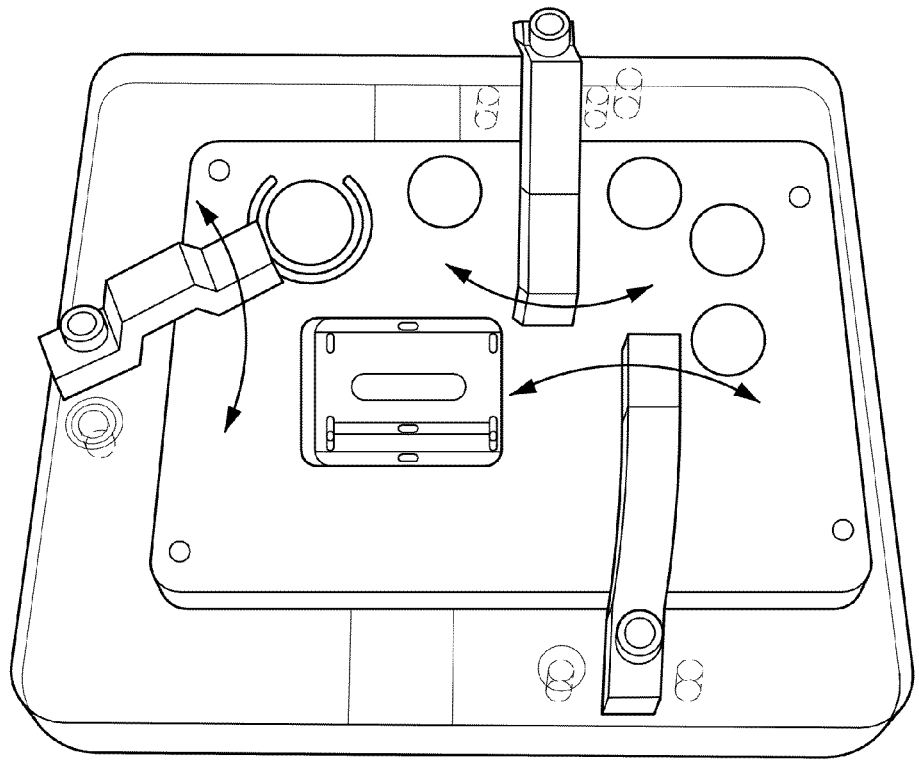
Figure 16C:
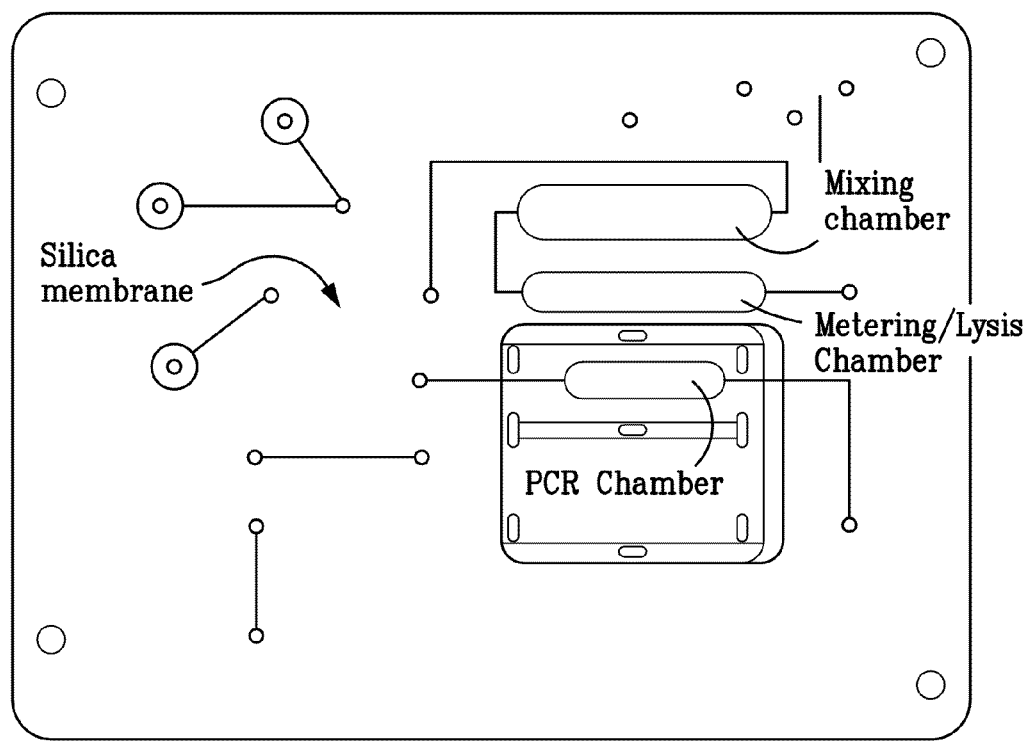
Figure 16D:
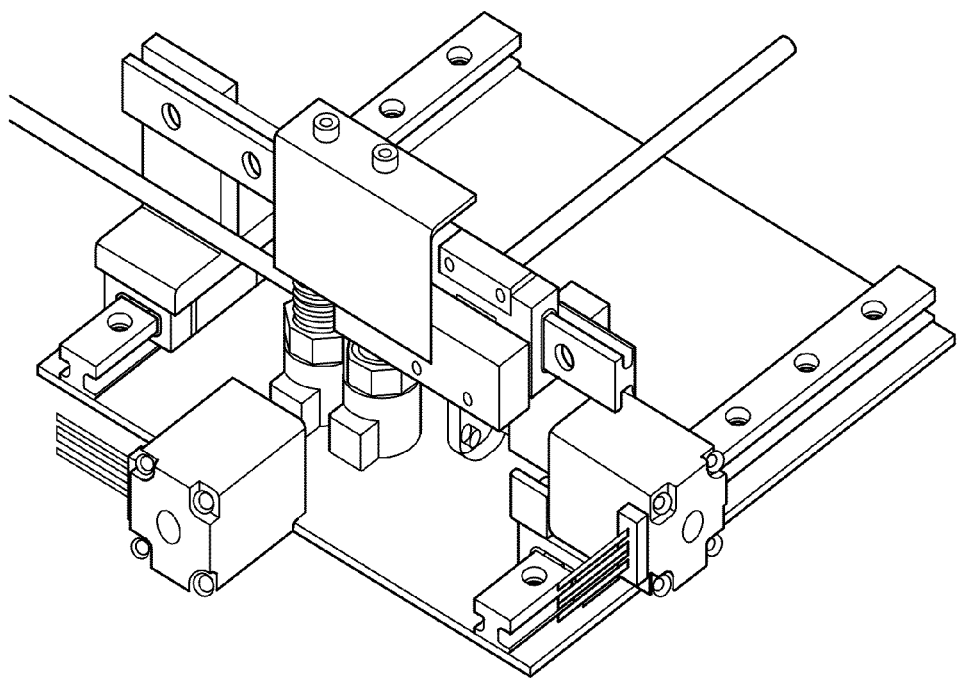

FIG. 14 is another non-limiting embodiment of the present invention. This figure shows a silica membrane-based cassette used in PCR amplification, with various modules (binding reagent, lysis reagent, washing buffers, and the like) disposed on the cassette. One or more of the modules may be covered by a sealing layer, as described elsewhere herein, which sealing layer is partially peeled back (or even entirely removed) to expose the sealed modules. An upper layer—which may have channels etched thereon—may then be placed over the unsealed modules and then itself sealed such that the channels in the upper layer place the modules in fluid communication with one another. The process flow in this non-limiting embodiment includes introduction of a cell-containing sample, cell lysis, isolation and PCR amplification of certain material, and detection of labeled, amplified material. Such a system allows for integration of lysis, isolation, and PCR on a single cassette, and the silia-chaotrope methods of lysis are applicable to viral and bacterial DNA and RNA. The cassette also allows for on-cassette storage of reagent—facilitated by the disclosed sealing layers—and can be used with a variety of detection modalities.

FIGS. 16A-D are other, non-limiting embodiments of the present invention, and illustrate the disposition of various pouches and bladders on a cassette. As described elsewhere herein, the pouches may be sealed and then placed into fluid communication with one another. Valves, pouches, and the like may be actuated by mechanical means, such as the manual valve actuator shown in the figure, or even by an X-Y moveable stage that is controllably positioned above one (or more) pouches or valves and then actuates the pouch or valve with a controllable piston, lever, or other device.

Figure 17A:
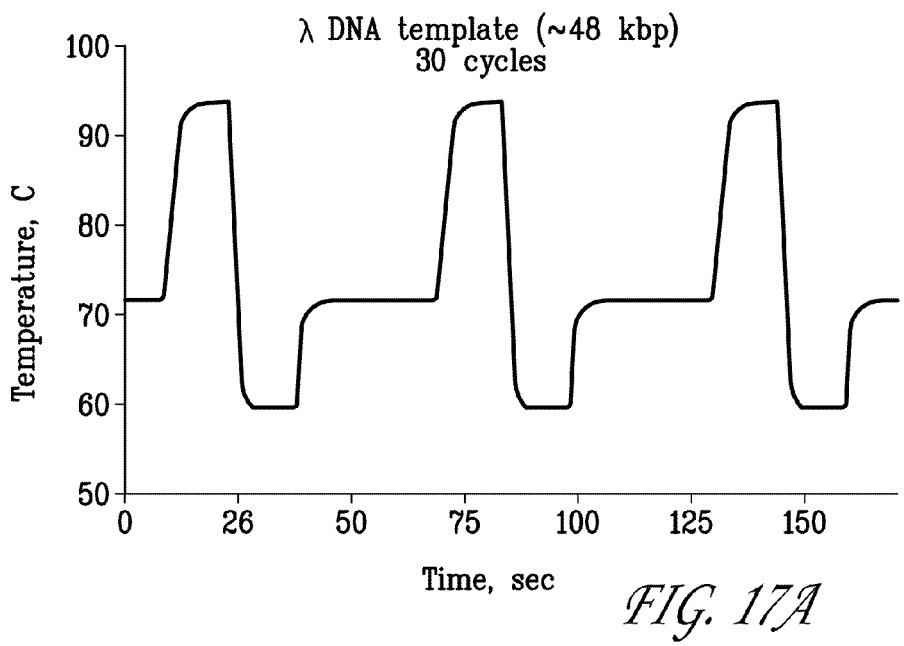
FIGS. 17A-C depict a dual-heater PCR reaction scheme on a cassette according to the claimed invention.
Figure 17B:
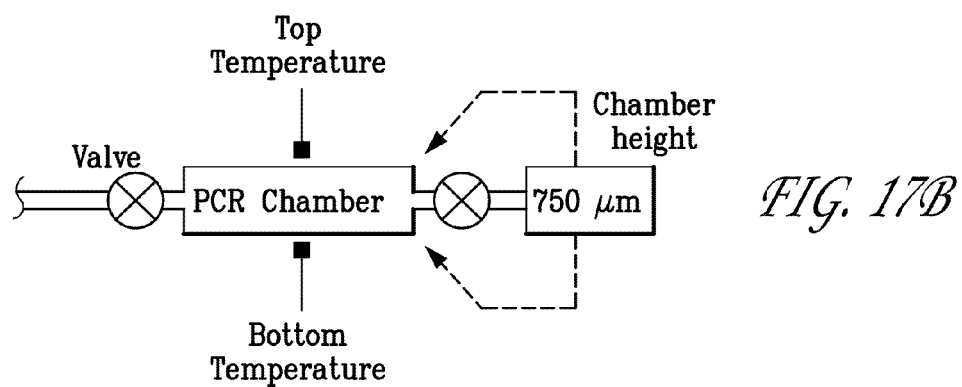
Figure 17C:
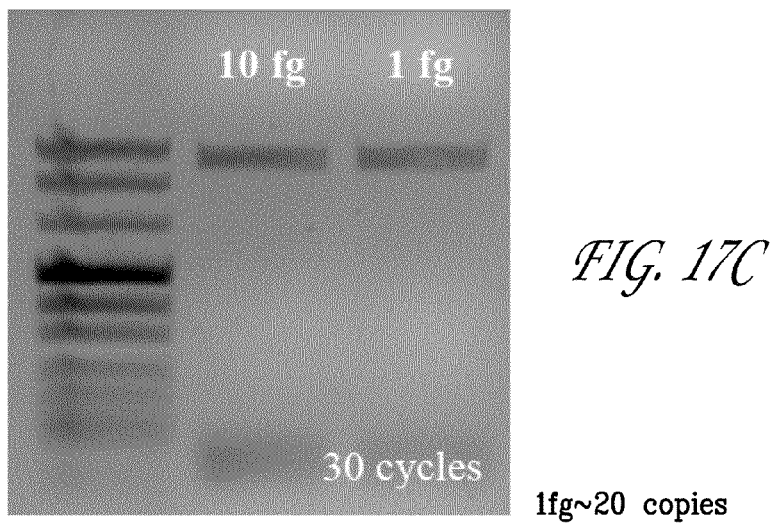

FIGS. 17A-C illustrates a exemplary temperature profile achieved by a dual-heater PCR device in conjunction with a PCR cassette according to the claimed invention. As shown, the heaters enable multiple heating cycles of the PCR reaction; the heaters may be disposed above and below the PCR chamber, as shown in the figure. The chamber can be of varying heights—the chamber shown is 750 microns in height, but taller and shorter chambers can be used, depending on the needs of the user.

Figure 18A:
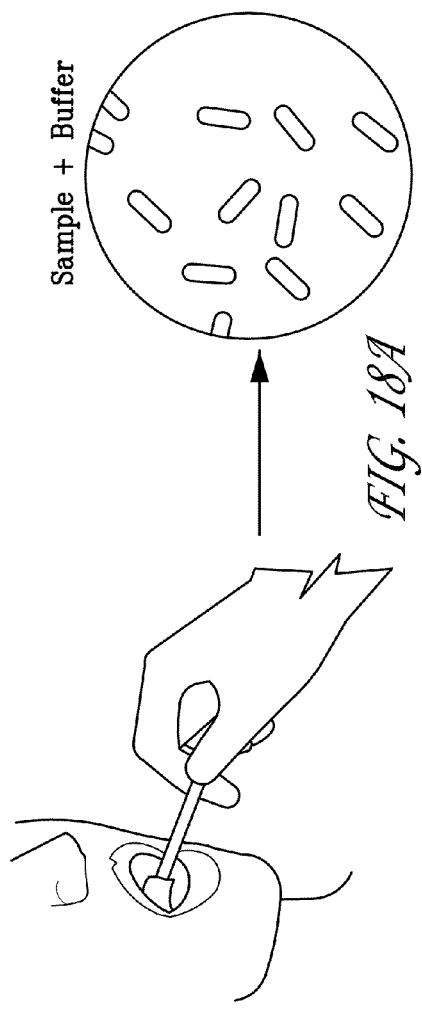
FIGS. 18A-C depict a single-step lysis, DNA isolation, and PCR analysis.
Figure 18B:
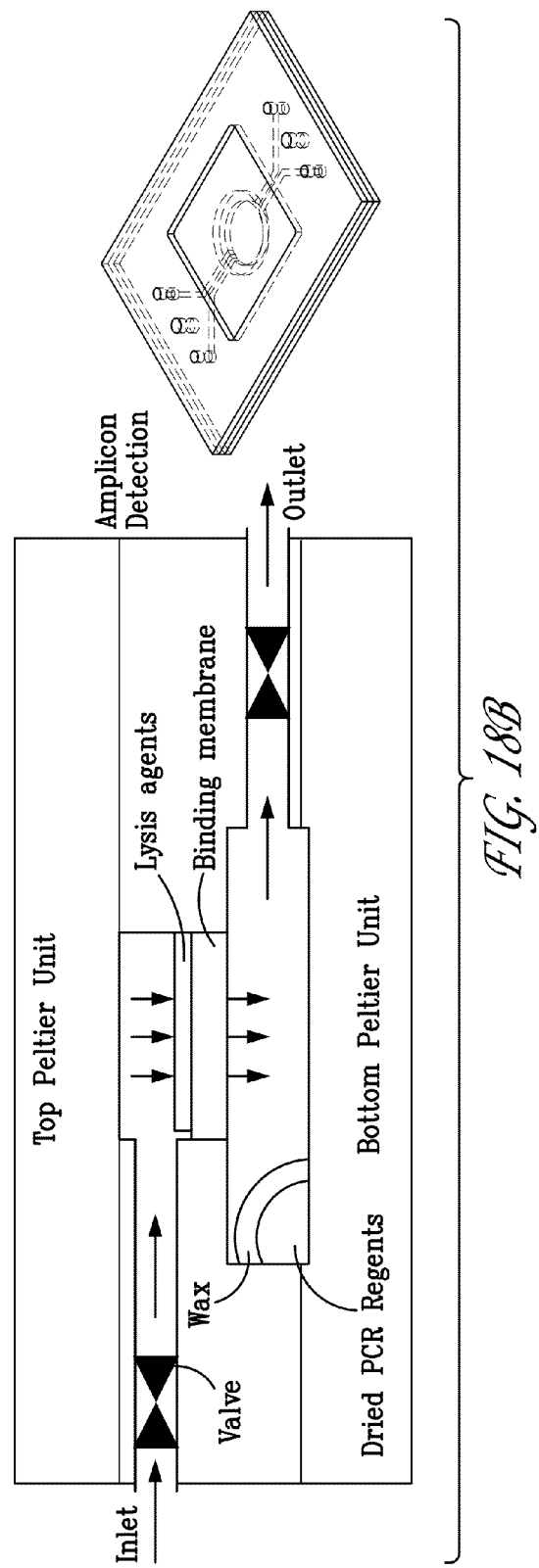
Figure 18C:
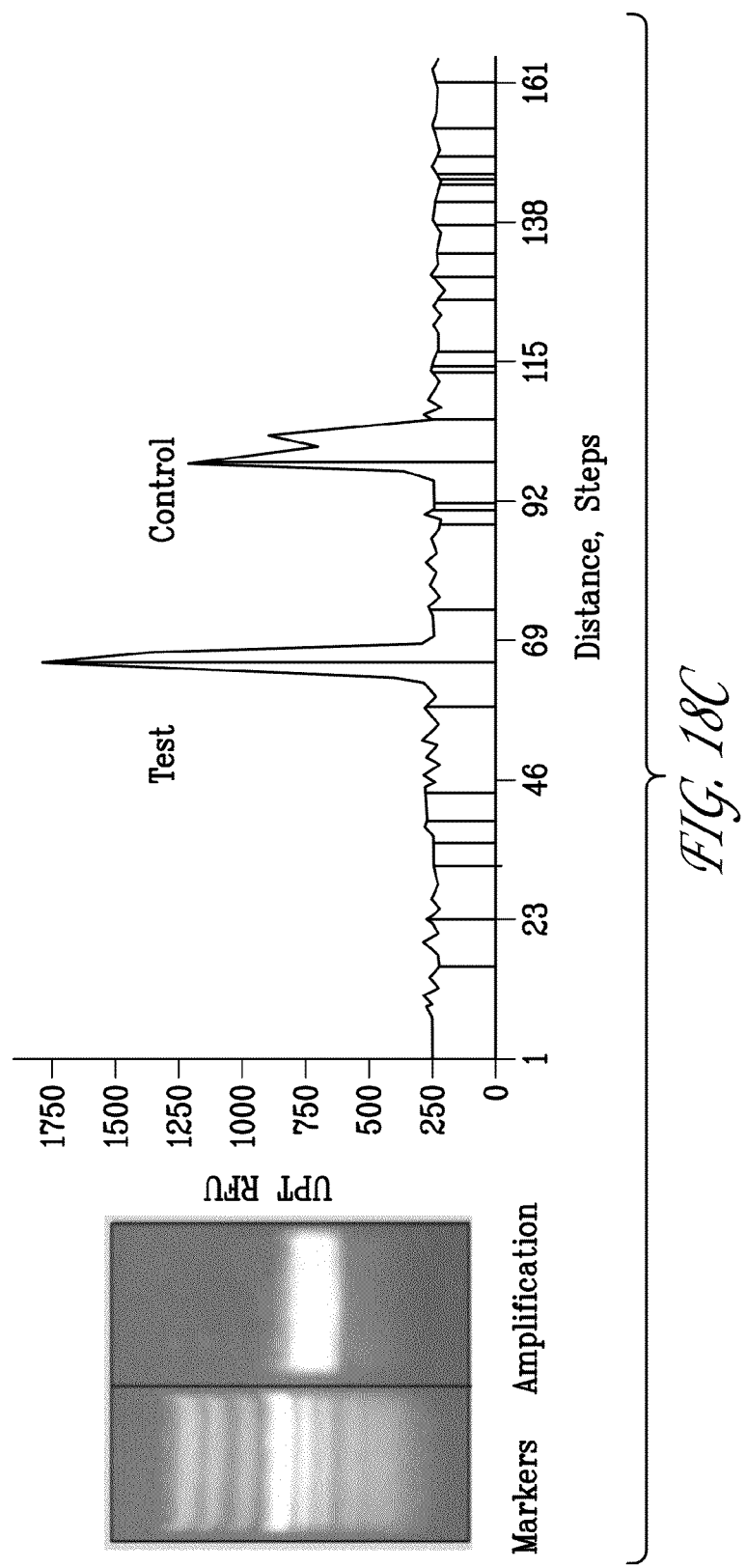

FIGS. 18A-C illustrate a single-step lysis, DNA isolation, and PCR device. As shown in the cut-away view, a sample passes across lysis agents and a binding membrane, into a PCR chamber for amplification, and then into a detection region. As shown in the figures, the system was capable of distinguishing between test and control samples.

Examples and Non-Limiting Embodiments

The following includes descriptions of sample, non-limiting embodiments of the present invention.

Overview

A hand-held, point-of-care, disposable, self-contained, immunoassay cassette comprising air pouches for pumping, a metering chamber, reagents storage chambers, a mixer, and a lateral flow strip was designed, constructed and tested. The assay was carried out in a consecutive flow format. The detection was facilitated with labels consisting of up-converting, phosphor (UCP) particles. The automated, timely pumping of the various reagents was accommodated with a spring-loaded timer. The utility of the cassette was demonstrated by detecting antibodies to HIV in saliva samples and haptenized PCR amplification products. The cassette has several advantages over dip sticks such as integrated storage of reagents and automated operation that reduces operator's errors and training. The cassette exhibited similar performance to that of the OraQuick Advance Rapid HIV ½ Antibody Test™. The cassette and actuator described herein can readily be extended to detect biomarkers of other diseases in body fluids and other fluids at the point of care.

Example

The detection system consists of a disposable, single use cassette and a timer-actuator. The cassette houses the various reagents and the detection strip. The timer-actuator provides mechanical actuation to pump the fluids through the cassette. There is no exchange of fluids between the timer-actuator and the cassette. In the embodiment described here, the timer-actuator can operate sequentially with multiple cassettes. Since the timer-actuator is inexpensive, one can envision an alternative embodiment of the cassette being integrated with the timer-actuator to form a single use, disposable system.

The Immunoassay System

In one non-limiting embodiment, an immunoassay system was constructed. The detection system consisted of a disposable, single use cassette and a timer-actuator. The cassette housed the various reagents and the detection strip, and a timer-actuator provided mechanical actuation to pump the fluids through the cassette. There was no exchange of fluids between the timer-actuator and the cassette. In the described embodiment, the timer-actuator operated sequentially with multiple cassettes. The cassette may, in some embodiments, be integrated with the timer-actuator to form a single use, disposable system.

The Cassette

The cassette had two states: a "storage state" in which the reagents' compartments are sealed and an "activated state" in which the reagents' compartments were connected to the various conduits. To activate the cassette, it was necessary to manually remove a sealing layer and replace that removed layer with a cover film that contained connecting conduits. The cover film was permanently affixed to the cassette to guarantee appropriate alignment of the connecting conduits with the various pores in the cassette, although detachable cover films are within the scope of the invention.

Figure 1D:
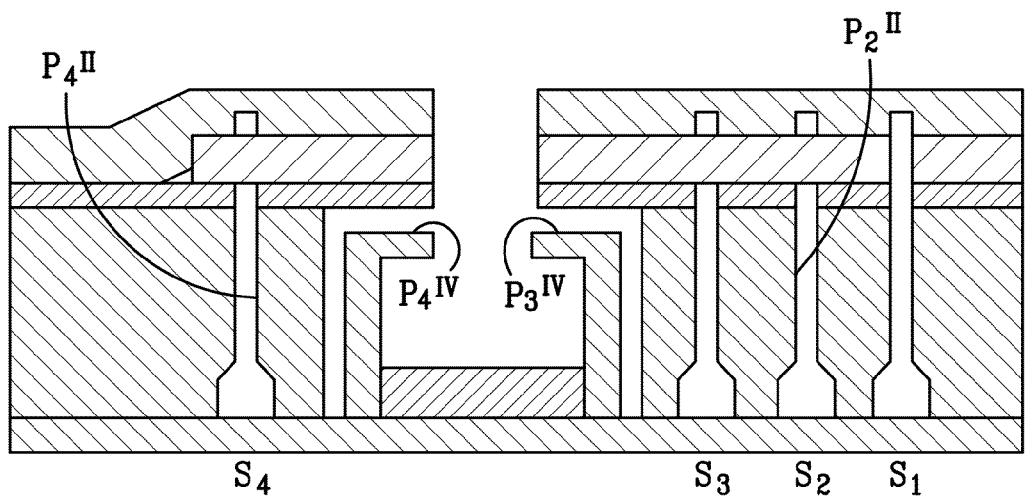
Figure 1E:
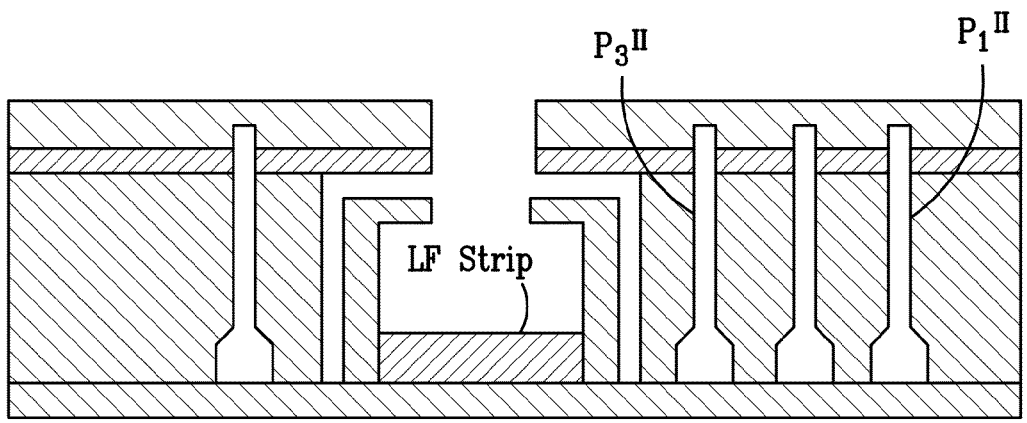
Figure 2:
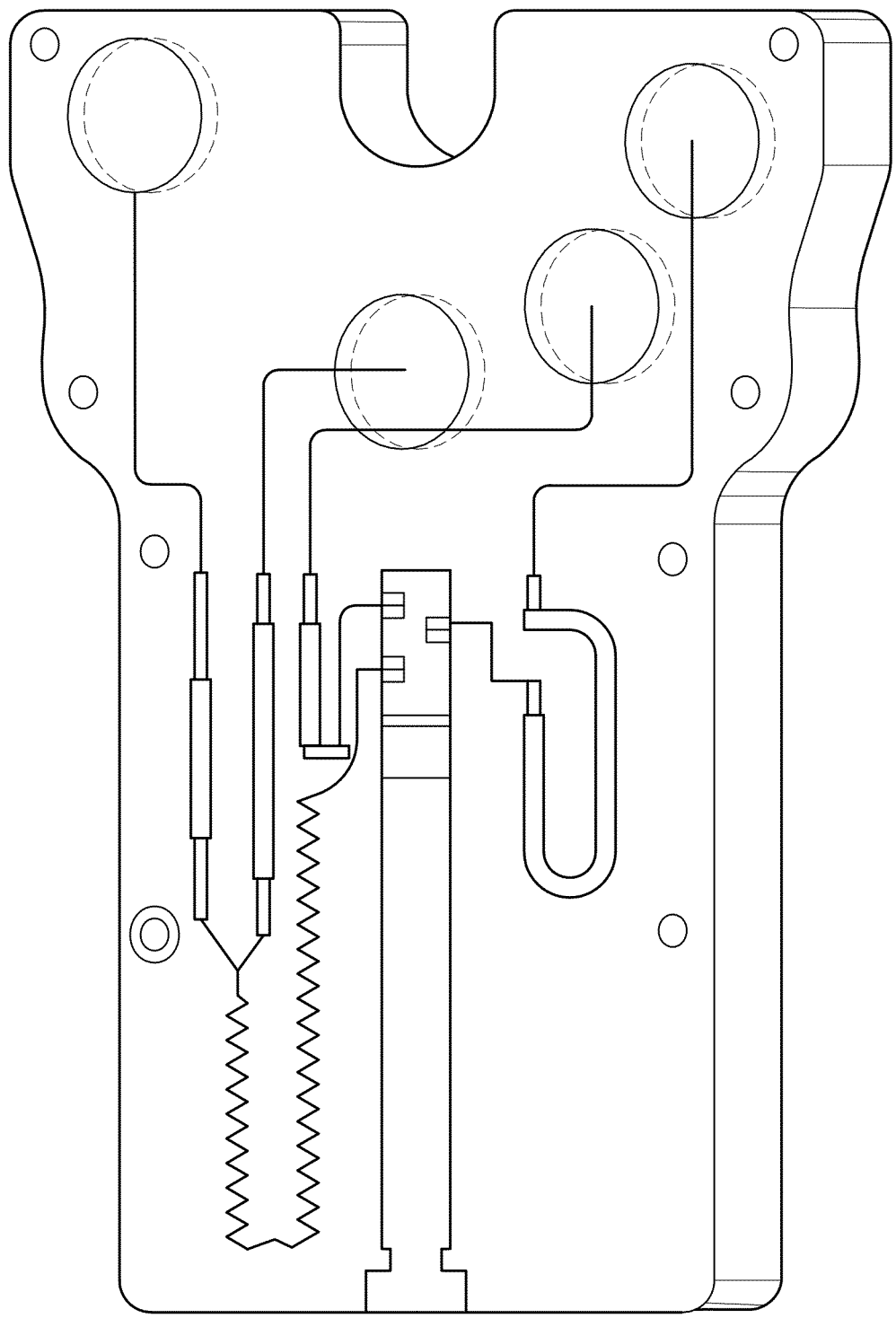
FIG. 2 illustrates an actual cassette according to the present invention.

The described cassette is depicted schematically in FIG. 1. FIG. 1a, 1b, 1c, 1d, and 1e are, respectively, a top view of the cassette; cross-section A-A along the length of the cassette in its "storage" (pre-activation) state; cross-section A-A of the cassette after its activation (the "activated state"); cross-section B-B along the width of the cassette prior to the cassette's activation; and cross-section B-B post cassette's activation. The positions of the cross-sectional cuts are shown in FIG. 1a. FIG. 2 is a photograph of the assembled cassette in its actuated mode. In FIG. 2, the various storage chambers are filled with food coloring for better visibility.

The main part of the cassette consisted of a 94 mm×58 mm, 5.84 mm thick polycarbonate (PC) sheet (FIG. 1c). To fabricate prototypes, a computer, numerical control (CNC) milling machine (HAAS Automation Inc., Oxnard, Calif.) was used. Cassettes could also suitably be formed by injection molding or other techniques known in the art. The top surface of the PC contained air pouch wells (denoted P1-P4 in FIG. 1a), inlets and exits of connecting, vertical vias, and a lateral flow (LF) strip chamber. The bottom surface of the polycarbonate sheet contained air and liquid conduits (FIGS. 1b and 1c), a sample metering chamber (S1), reagent storage chambers (S2-S4), and mixing chamber (shown by the zigzag path). The conduits had square cross-sections with widths and depths ranging from 250 μm to 500 μm and the storage chambers had vaulting cross-sections with 1.6 mm widths and 1.60 mm depths, although chambers of different cross-sections were considered suitable. The chambers formed in the bottom layer were connected to the top surface with 500 μm diameter vertical vias.

The conduits in the bottom layer were capped with a 120 μm thick polycarbonate film (FIGS. 1b and 1c), which film was thermally bonded to the polycarbonate sheet. The air pouch wells (P1-P4) were capped with a 100 μm thick, flexible natural latex rubber film (McMaster-Carr, New Brunswick, N.J.). The latex film was attached to the polycarbonate with the aid of double sided adhesive tape (McMaster-Carr, New Brunswick, N.J.), although other ways of attaching the film—e.g., glue, thermal bonding—are suitable.

During storage (FIG. 1b), all the chambers (with the exception of the metering chamber) were hermetically sealed with the sealing film located on the top surface of the polycarbonate sheet (FIG. 1b). The sealing film allowed sample introduction into the metering chamber and the flow of excess sample into the waste chamber. The waste chamber was located within the sealing layer. The chambers stored the various reagents needed to carry out the immunoassay and were pre-filled during the cassette manufacturing phase. Chambers S1, S2, S3, and S4 were, respectively, the metering chamber, the lateral flow buffer storage chamber, the wash solution storage chamber, and the labels' solution storage chamber.

Subsequent to the sample introduction, the sealing layer was peeled off and replaced with a "connecting" cover film (FIG. 1c). The connecting cover film was made of polyester film in which conduits were machined with a $CO_2$ laser. The flexible connecting cover was permanently attached to the PC cassette to assure appropriate alignment of the connecting conduits with the various vias. Once attached to the double sided tape affixed to the polycarbonate sheet, the conduits in the cover film formed connections between the air conduits' ends (denoted $P_i^I$) and the chambers' inlets (denoted $P_i^{II}$) and between the chambers' exits (denoted PiIII) and the downstream conduits leading to the lateral flow strip (denoted $P_{ii}$'). In the above, i=1, 2, 3, and 4 indicate that the vias are associated, respectively, with conduits leading from pouches 1, 2, 3, and 4.

The cassette consisted of four functional regions: (i) the pumping region containing the air pouches, (ii) the storage and metering chambers region, (iii) the stirrer, and (iv) the detection region (the lateral flow strip).

During operation—and after to sample introduction—pouches P1 and P2 were compressed simultaneously. The air from pouches P1 and P2 displaced, respectively, the sample and the lateral flow buffer into the "zigzag" stirrer, in which location where the sample mixed with the lateral flow buffer. Subsequently, the sample-buffer blend was discharged onto the lateral flow strip and migrated up the strip by capillary forces. The strip included test zones with immobilized ligands that bound specifically to the target analytes in the sample and a control zone that binds the labels that passed through the test zone.

After a predetermined time interval, pouch P3 was compressed to discharge the wash solution into the strip to remove any unbound analytes. A few minutes later, pouch P4 was compressed to discharge the buffer containing the functionalized labels. This non-limiting example used upconverting phosphor particles UCP for immunolabeling. A cassette according to the present invention could accommodate other labels as well such as gold particles, quantum dots, and fluorophores.

The Timer-Actuator

Figure 4A:
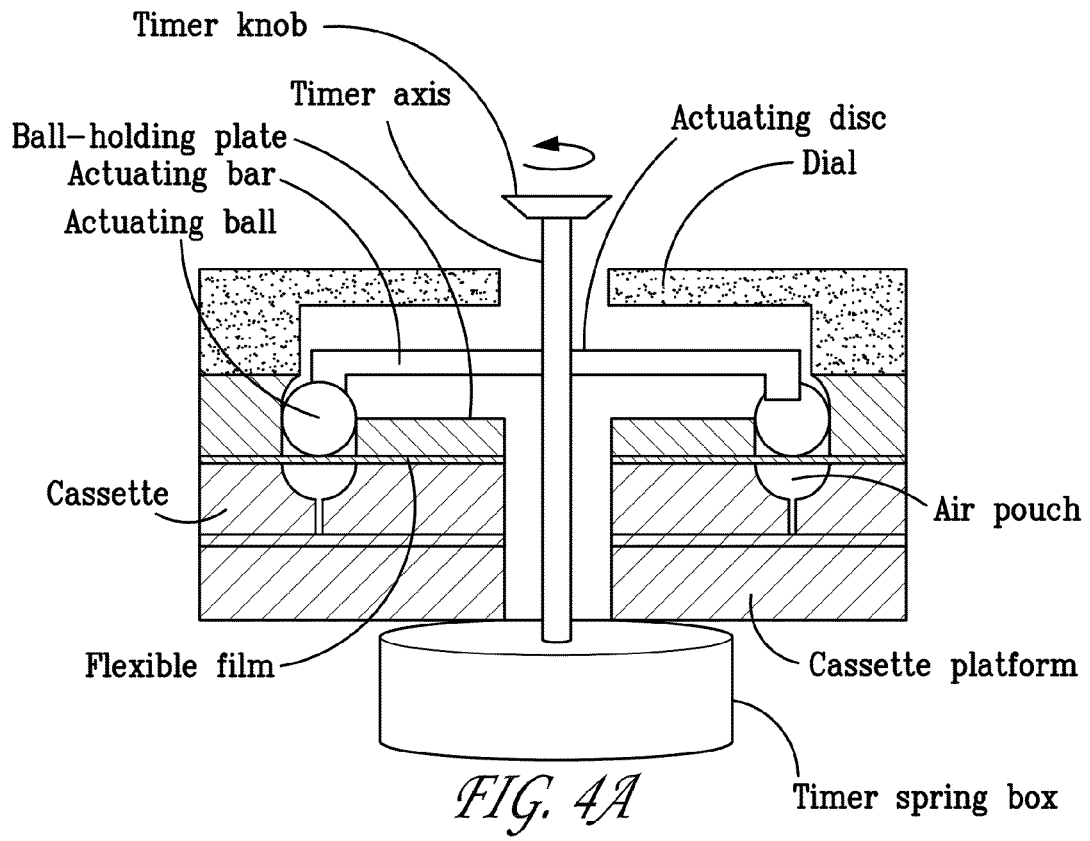
FIG. 4 illustrates a schematic view of the operation of an analytic device according to the present invention.

FIGS. 3 and 4 are, respectively, a photograph and a schematic depiction of the actuation mechanism. Subsequent to the sample loading, the cassette was docked in the timer-actuator. The cassette was aligned so that the air pouches were located beneath the actuating balls (FIG. 4a).

The actuation mechanism consisted of a dial, actuating disc, ball-holding plate, cassette socket, cassette platform, and spring-driven actuator-timer. For the immunoassay test described here, we used a timer with a time span of 15 minutes (McMaster-Carr, New Brunswick, N.J.). The actuating disc with two protrusions (shaped like isosceles triangles of 5 mm length×6 mm width×3.7 mm height) was mounted to the timer's rotating shaft. The actuating protrusions on the disc rotated with the timer's shaft and pressed against the balls caged in the ball-holding plate at the appropriate time. The ball-holding plate had four holes with diameters of 9.6 mm, in which four actuating plastic balls with diameters of about 9.5 mm were caged. By adjusting the inclination angles of the protrusions the flow rates of the various reagents could be adjusted. Once the air pouch was compressed, the compressed air displaced the liquid from the storage compartment and forced it downstream.

Stirrer

Figure 5A:
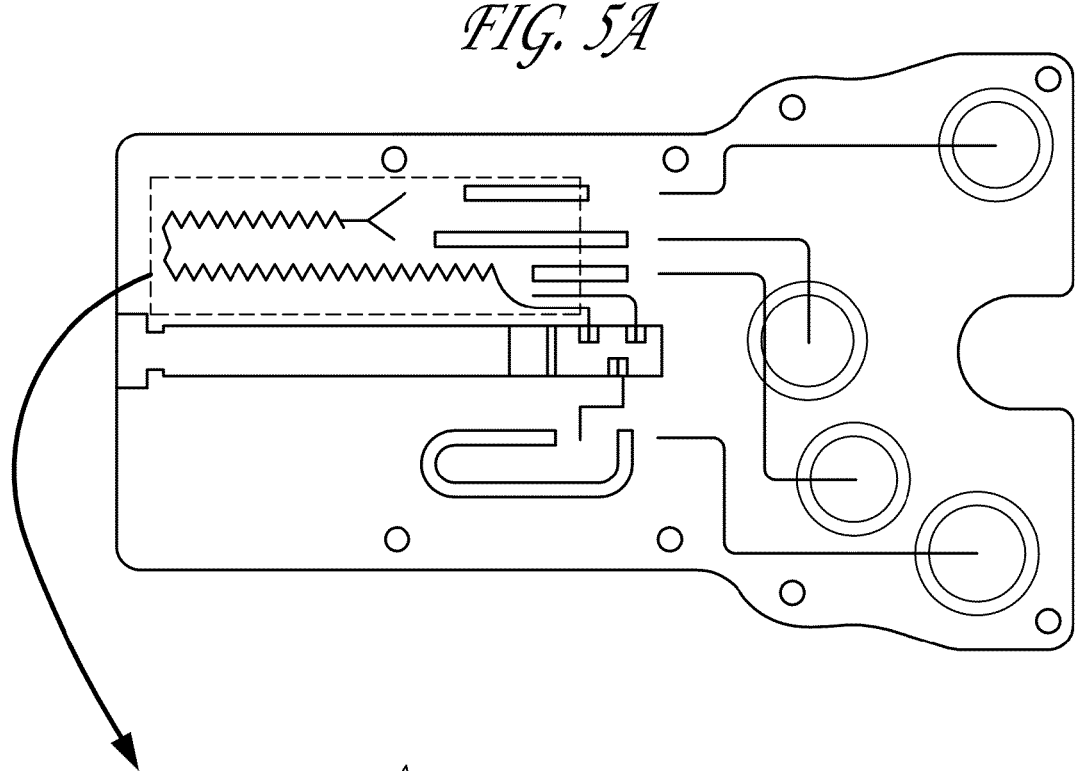
FIG. 5 illustrates a cassette according to the present invention, including a zig-zag mixing channel.
Figure 5B:
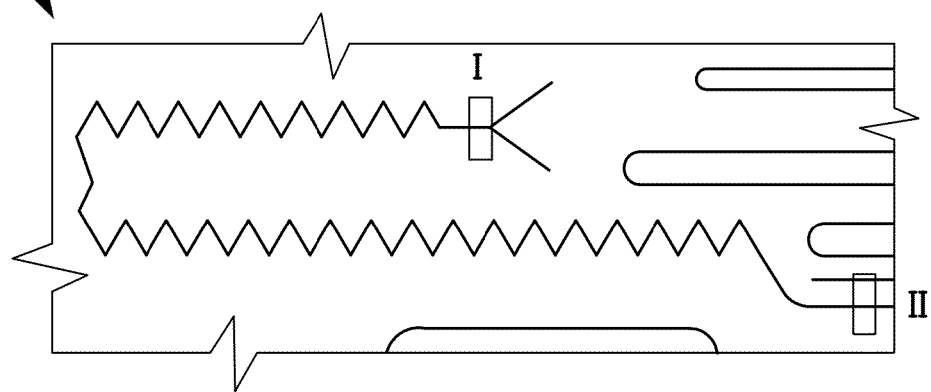

Because turbulent flows are difficult to generate in microfluidic systems with conduit sizes on the order of hundreds of micrometers, it was considered advantageous to induce secondary flows to enhance mixing. This example relied upon a zigzag channel mixer, in which the sample and lateral flow buffer flowed concurrently. FIG. 5 shows the stirrer module. FIG. 5a shows the position of the stirrer in the cassette and FIG. 5b zooms on the stirrer component of the cassette.

In addition to providing a long path to accommodate the diffusion process, the bends in the conduit induced secondary flows that enhanced mixing. The LF immunoassay protocol dictated a sample volume of 10 µL and LF buffer of 40 µL. To accommodate these vastly different volumes, the system utilized different size air pouches for the sample and the lateral flow buffer.

To evaluate the stirrer's performance, rhodamine 123 fluorescence dye in LF buffer solution was used to mimic the sample. The mixing process was observed under a fluorescence microscope and recorded with a CCD camera.

Figure 6:
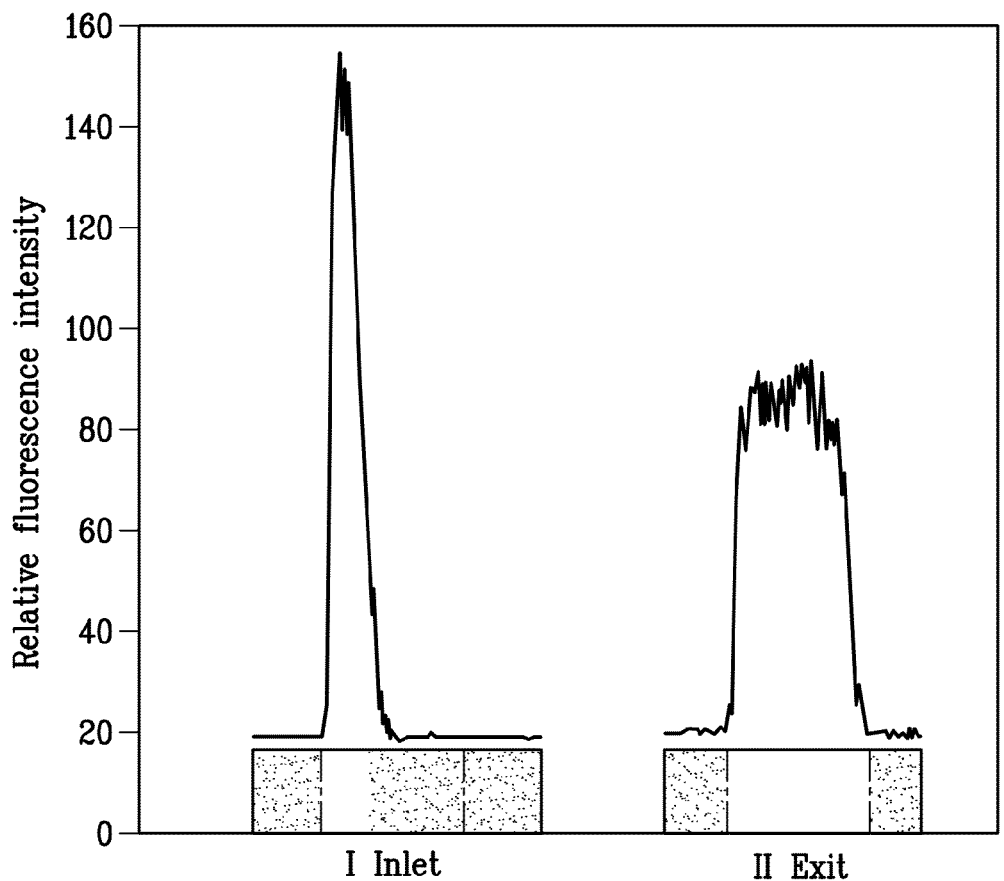
FIG. 6 illustrates fluorescence images and the fluorescent intensity as functions of position along a conduit of a cassette according to the present invention.

FIGS. 6a and b show the fluorescence images and the fluorescent intensity as functions of position along the conduit's width at the inlet (I) and exit (II) regions (the framed regions in FIG. 5b) of the zigzag conduits. The vertical, dashed lines in FIG. 6 identify the conduit's edges. At the inlet the dye occupies only part of the conduit's width and the two solutions are well separated with a nearly sharp interface. In contrast, at the exit, the dye is spread nearly evenly across the width of the conduit indicating good mixing.

To quantify the mixing process, the standard deviation of dye intensity is defined:

$$\sigma = \sqrt{\frac{1}{W}\int_0^W (I(y) - \bar{I})^2 \, dy}$$

In the above, $\bar{I}$ is the average of the dye intensity across the conduit's width. When the two fluids are well-separated, $\sigma$ will approach 1. For example, when the dye occupies half of the conduit's width at uniform intensity, $\sigma \sim 0.71\,\bar{I}$. When the two fluids are well mixed and the dye intensity is nearly uniform across the conduit's width, $\sigma \to 0$.

Figure 7:
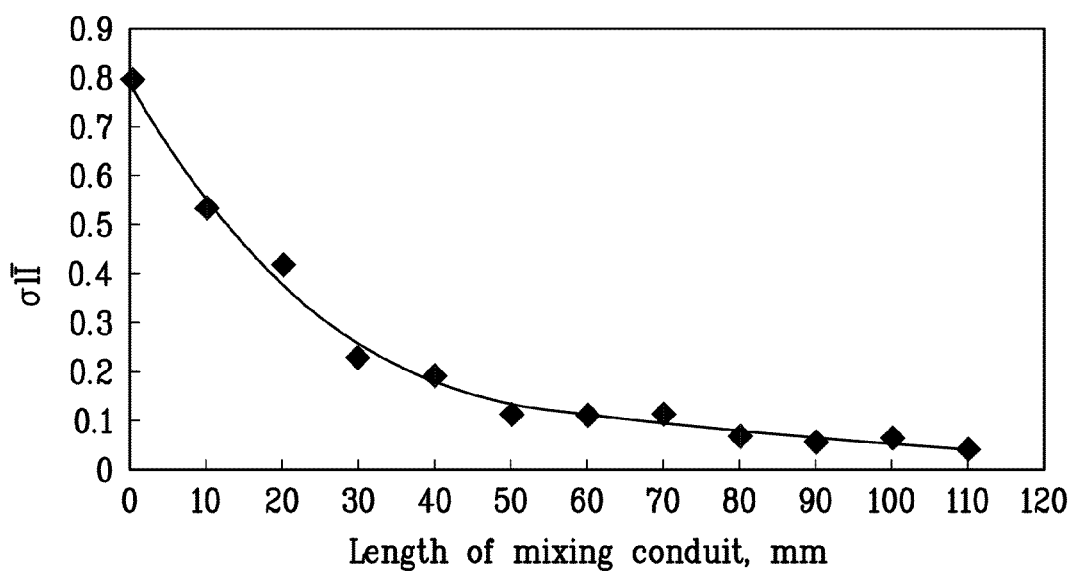
FIG. 7 illustrates depicts the normalized standard deviation σ/I as a function of the axial distance along the stirrer's length when the Reynolds number (based on the conduit's hydraulic diameter) is about 5.

FIG. 7 depicts the normalized standard deviation $\sigma/\bar{I}$ as a function of the axial distance along the stirrer's length when the Reynolds number (based on the conduit's hydraulic diameter) is 5. Without being bound to any particular theory, it was seen that $\sigma/\bar{I}$ decreased nearly exponentially, asymptotically approaching the value of zero and showing the effectiveness of mixing by the zigzag stirrer.

Reagents and Protocols

These embodiments tested two different analytes; the OraQuick ADVANCE Rapid HIV-½ Antibody Test Kit Controls that consisted of a sample of HIV antibodies and a 305-bp DNA fragments with 5'-Dig hapten on one strand and 5'-Bio hapten on the opposite strand. The HIV antibodies were sprinkled in saliva and the DNA fragments were suspended in water. The former was used to demonstrate the ability of the cassette to detect the presence of the HIV virus in saliva. The latter enabled a dilution series to obtain quantitative information regarding the device's performance.

In both cases, the immunoassay protocol consisted of three, consecutive flow steps: (i) 10 µL sample (saliva or PCR amplicons) were mixed with 40 µL LF buffer, then flown through strip; (ii) after 2 minutes, 20 µL LF buffer was blotted onto the strip to wash any unbound analytes; and (iii) 2 minutes later, 80 µL LF buffer with 100 ng UCP conjugate were added to the LF strip to label the immunoassay.

The HIV saliva samples were provided by the College of Dentistry at New York University (New York 10010, USA). The lateral flow buffer consisted of 100 mM Hepes (pH 7.2), 270 mM NaCl, 0.5% (v/v) Tween-20, and 1% (w/v) BSA. The immuno labeling buffer was, respectively, a mixture LF buffer with protein A-coated UCP (UCPprot A) reporter particles for HIV and avidin-conjugated UCP reporter particles for haptenized DNA.

The LF strips were supplied by OraSure Technologies, Inc. (Bethlehem, Pa.) and comprised a nitrocellulose part (20 mm, SRHF04000, Millipore) with a sample loading pad (10 mm, glass-fiber No. 33, Schleicher & Schuell) at the upstream end and an absorbent pad (20 mm, paper No. 470, Schleicher & Schuell) on the downstream end. The HIV LF strip had a "test-line" containing immobilized synthetic peptides representing the HIV envelope region to capture HIV antibodies and a "control line" consisting of immobilized goat anti-human IgG to verify the successful migration of the labels (functionalized with protein A) up the strip. The nitrocellulose of the DNA LF strips contained a capture line of avidin-D and control line consisting of a goat anti-mouse IgG antibody.

The DNA samples were produced by lysing B. cereus cells, isolating the (genomic) DNA with QIAGEN DNeasy™ Tissue Kit (QIAGEN Inc., Valencia, Calif. 91355), and using the eluted genomic DNA as the PCR template. The PCR reagents were 50 mM Tris-HCl (pH 9.0), 1.5-3.5 mM MgCl2, 200 µM dNTP, and 0.1 µg/µL BSA. The forward and reverse primers used at 0.3 µM were, respectively, (5'-TCT CGC TTC ACT ATT CCC AAG T-3') and (5'-AAG GTT CAA AAG ATG GTA TTC AGG-3'); at the 5'-end primers were provided with a Biotin (Bio) or a Digoxinenin (Dig) hapten, respectively. The primers targeted a 305 bp specific gene fragment.1 The DNA amplification was initiated with a denaturation step at 95° C. for 120 sec, followed by 25 amplification cycles (95° C., 20 sec; 55° C., 30 sec; 72° C., 23 sec), and terminated with an extension step at 72° C. for another 120 sec on PCR thermocycler (Techne Incorporated, Princeton, N.J.). Haptenized DNA concentration of initial PCR products were determined using NanoDrop ND-1000 spectrophotometer (NanoDrop Technologies, Wilmington, Del.) and was diluted to a series of sample with DI water for immunoassay.

A UCP Reader (UPlink, Orasure Technologies, Inc., Bethlehem, Pa. 18015), adapted with a 980-nm infrared laser, excited the UCP particles and recorded the 550-nm emission, which corresponds to the green light spectrum of the particular UCP phosphor particles used here. The IR light was guided with a fiber bundle through a focusing lens. The same fiber bundle collected the light that was emitted by the IR-excited, UCP particles. To facilitate the scanning of the lateral flow strip, the reader was equipped with a microstepper motor for position control. The UPlink system's software controlled the scanner movement, laser excitation, signal reception, and data collection, processing and display. The emission signal was guided through a 550 nm band-pass filter appropriate for the emission wavelength of the UCP particles. The signal was then processed by a photomultiplier and was reported as relative fluorescence units (RFU) as a function of position along the strip.

Results and Discussion

Cassette Operation

First, the analyte sample (saliva sprinkled with HIV antibodies or haptenized DNA) was inserted into the 10 µL metering chamber. Excess sample was discharged into the waste chamber located in the sealing film (FIG. 1b). Next, the sealing film was peeled off from the double-sided tape and the flexible cover film was lowered and affixed onto the double-sided tape to join the air pouches through the strip connecting conduits with the storage chambers on the one hand and the storage chambers with the lateral flow strip on the other hand. Because the flexible cover film's position was predetermined through the attachment of its edge to the PC cassette, good sealing and alignment were achieved without alignment pins. Finally, the immunoassay cassette was inserted into the timer-based actuator for sample mixing and reagent pumping. Once inserted in the actuator, the operation proceeded in a fully automated fashion.

Actuation Mechanism of Timer-Based Actuator

The cassette was actuated with the timer-actuator (having a maximum time interval of 15 minutes and maximum displacement angle of 308.55°). To realize mixing, two protruding bars of the actuating disc pressed the two balls that, in turn, compressed the air pouches of the sample chamber and buffer chamber to simultaneously discharge the sample and buffer into the zigzag channel for online mixing. The displacement angles of the other two balls were 41.14° each, corresponding to time intervals of 2 minutes (consistent with the HIV immunoassay protocol).

Figure 4B:
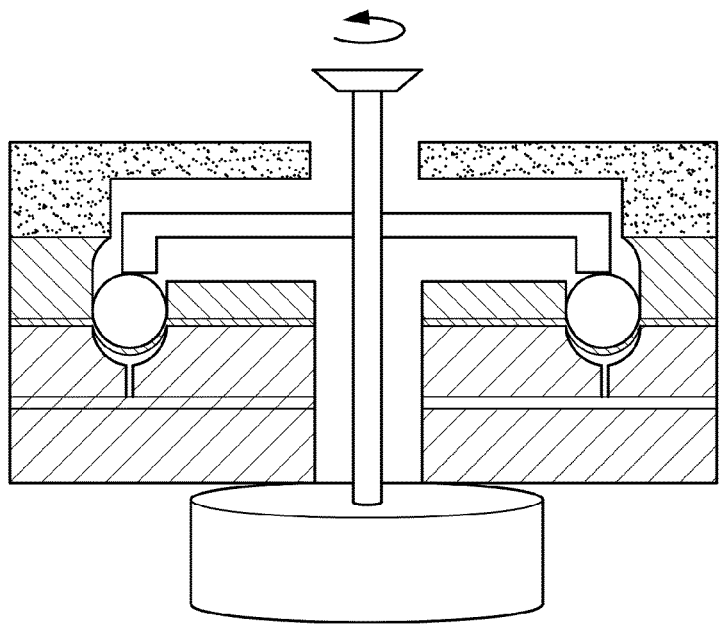

The operation of the actuator is illustrated in FIG. 4. At the beginning of the operation, the protrusions were displaced away from the actuating balls (FIG. 4a). The timer rotated the actuating disk counter-clockwise and brought the two protrusions into contact with the two balls that actuated, respectively, the air pouch associated with the metering chamber and the air pouch associated with the lateral flow buffer chamber (FIG. 4b). The sample was mixed with the lateral flow buffer in the zigzag channel and pumped into the strip's chamber. Two minutes later, the actuating protrusion moved on top of the ball that actuated the air pouch associated with the wash buffer chamber, and pressed it down. As a result, the wash LF buffer was discharged into the strip's chamber. Two minutes later, the actuating protrusion pressed the last ball that actuated the air pouch associated with the UCP storage buffer chamber and the UCP suspension was discharged into the strip's chamber. Here, our timer-based actuator had two major functions: one is to automate to timing and another was to actuate the air pouches to pump sample and reagents into the strip chamber, Dead Volumes Cassettes filled with one reagent at a time (without a lateral flow strip) and empty cassettes (after the removal of the lateral flow strip) were weighed to estimate the dead volumes of all the storage chambers in the inventive devices. Saliva from a volunteer was used as the sample and pipetted into the metering chamber. The other chambers were filled with LF buffer. Each of the storage chambers was loaded separately, the cassette was weighted (with only one full storage chamber at a time), the contents of the selected storage chamber was discharged (using the same operations as one would use in the regular operation of the cassette) and the cassette (without the lateral flow strip) was weighted again. The dead volumes of the saliva sample-buffer mixture, wash buffer, and UCP-conjugate buffer were, respectively, smaller than 4.7%, 2.0% and 2.7%. Without being bound to any single theory, due to the long zigzag mixing channel, the sample-buffer mixture had the largest dead volume.

HIV Immunoassay

FIG. 8 depicts the results of the HIV test. FIG. 8a is a schematic of the lateral flow strip including a "test line" consisting of HIV-specific antigens and a control line functionalized with anti-human IgG to bind human IgGs functionalized to the UCP labels. Three groups of samples: negative, low positive, and high positive were tested. After incubation, the LF strip was removed from the cassette and then inserted into a standard UPlink reader (OraSure Technologies, Inc., Bethlehem, Pa.) equipped with a 980 nm IR laser exciter. (In the future, a smaller reader will be integrated with the actuator).

FIG. 8b depicts the fluorescence intensity of the negative, low positive, and high positive HIV samples in relative fluorescent units (RFU) as a function of the position along the strip. The areas under the peaks is proportional to the amount of target analyte(s). The negative signal yielded no test peak and a large control peak. The low positive sample yielded moderate height test and control peaks. The high positive sample yielded a high test peak and a low control peak. The tests were repeated numerous times with similar results.

Figure 9:
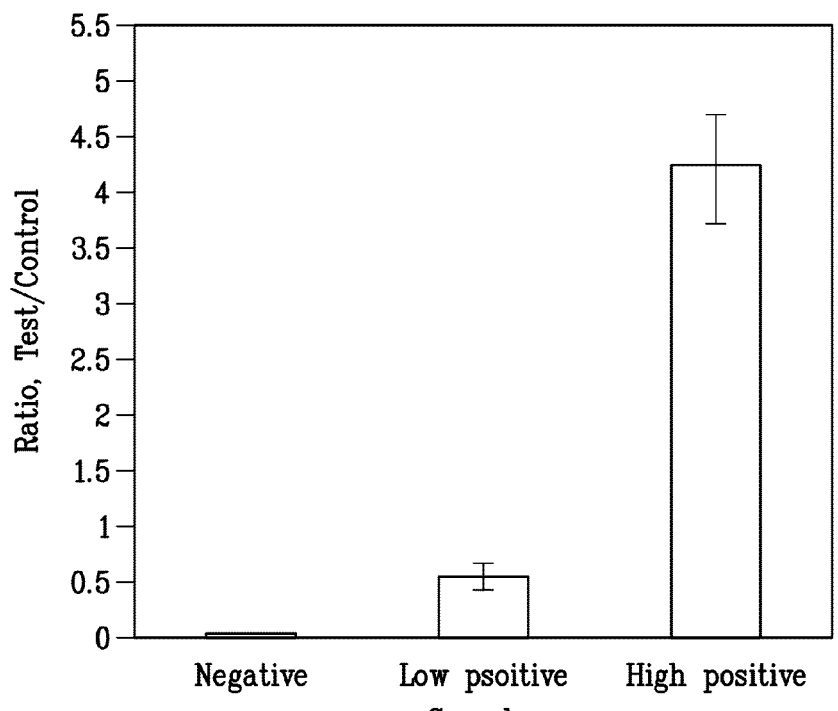
FIG. 9 illustrates depicts the ratio (T/C) of the areas of the test (T) and the control (C) signals for the test of FIG. 8.

FIG. 9 depicts the ratio (T/C) of the areas of the test (T) and the control (C) signals. As the HIV antibodies concentration increased, so did the ratio T/C. The ratios (T/C) of the negative, low positive and high positive samples are, respectively, 0.01, 0.5 and 4.3. Each bar represents the average of three independent measurements with three different cassettes. The scatter of the data is shown by the error bars.

Haptenized 305-bp DNA

Figure 10:
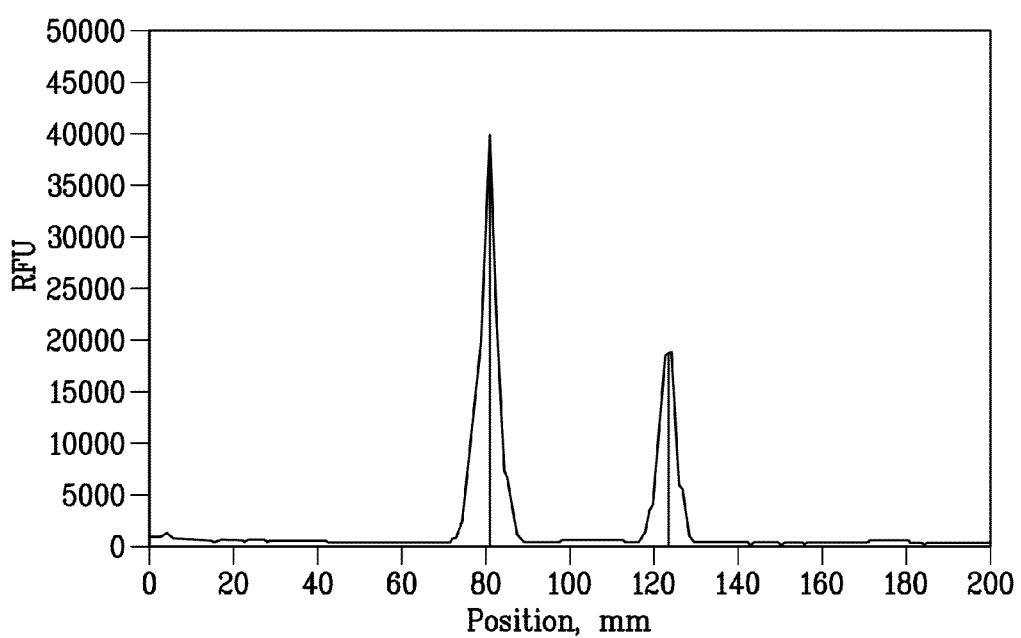
FIG. 10 illustrates depicts an example of the test and control peaks for the sample containing 1 ng of DNA for the test of FIG. 8.
Figure 11:
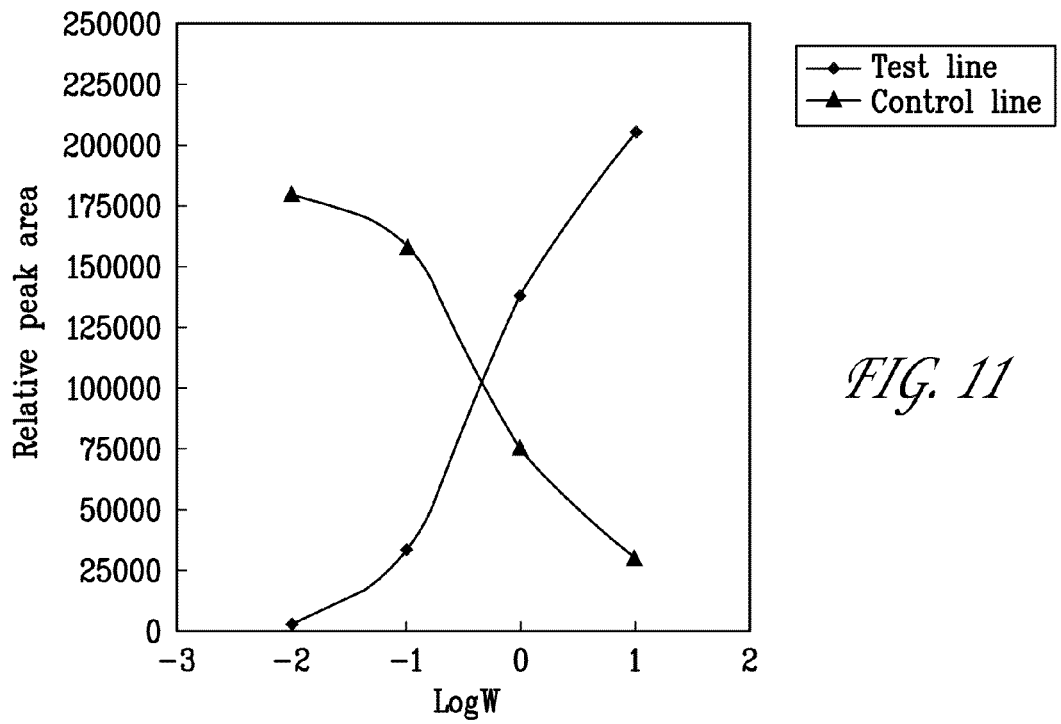
FIG. 11 illustrates the areas of the test (diamonds) and control (upright triangles) peaks as functions of the DNA concentration (W) for the test of FIG. 8.

To obtain quantitative data of the cassette's performance, we created 10 µl samples consisting of 0, 0.01 ng, 0.1 ng, 1 ng, and 10 ng haptenized DNA fragments of *B. cereus*. FIG. 10 depicts an example of the test and control peaks for the sample containing 1 ng of DNA. FIG. 11 depicts the areas of the test (diamonds) and control (upright triangles) peaks as functions of the DNA concentration (W). As the DNA concentration increased, the area of the test peak increased as well and the area of the control peak decreased. The figure suggests that DNA concentrations as small as 0.01 ng (~50 attomol) can be detected.

Figure 12:
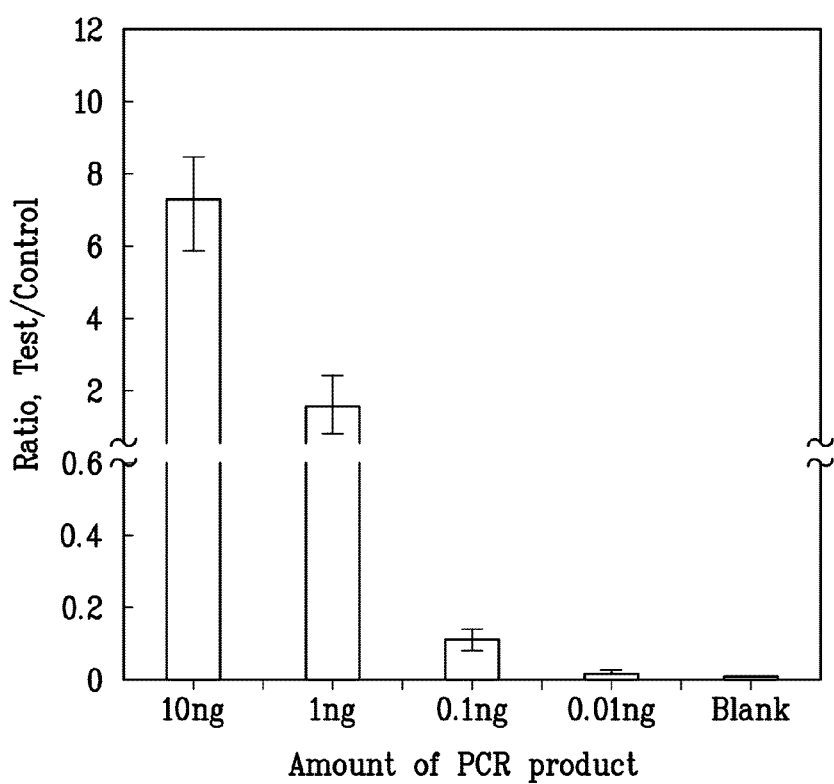
FIG. 12 illustrates the ratio of the test and control peak's areas (T/C) as a function of the DNA concentration for the test of FIG. 8.

FIG. 12 depicts the ratio of the test and control peak's areas (T/C) as a function of the DNA concentration. Each bar is the average of three independent experiments carried out with different cassettes. The scatter of the data is represented with the error bars. Not surprisingly, as the concentration of the DNA increased, the ratio T/C increased as well.

CONCLUSIONS

An easy-to-use, self-contained, inexpensive, disposable immunoassay cassette was developed and successfully tested. The cassette integrated reagent storage, sample metering, mixing, pumping, valving, and lateral flow strip assay steps. The system operated in an automatic fashion and did not require trained personnel. While the illustrative device described herein operated with a lateral flow strip as the ligand immobilization medium, with modifications, the cassette can accommodate other immobilization substrates such as beads functionalized with various ligands.

This particular example utilized up converting phosphor particles (UCP) as labels. The device can operate, however, with other labels such as gold particles, quantum dots, and fluorophores. Furthermore, other detection modalities such as electrochemical detection can be used as well.

The blending of the sample and buffer was accomplished with a zigzag stirrer, which provided adequate performance for our needs. Other passive stirrer geometries can be implemented as well.

A hand-held timer-based actuator was designed and fabricated to automate the actuation of the air pouches and to facilitate timely pumping of the sample and the stored reagents in a predetermined sequence such as dictated by consecutive flow, immunoassay protocol. In some cases, the timer-actuator may be integrated into the cassette to form a disposable, single-use system. The timer actuator can be spring-driven. The timer actuator can be replaced with a stepping motor for applications that require larger number of and more complicated processing steps than the ones required for the present application. Furthermore, in the future, a minute laser diode/photo diode reader will be integrated with the actuator to form a fully functional hand-held device.

The device's performance was demonstrated with the detection of antibodies to the HIV virus and the detection of haptenized DNA fragments of *B. cereus* suspended in saliva. With appropriate immobilized ligands, the device can be used for the detection of a variety of other proteins in a liquid sample such as other body fluids, water, and food.

What is claimed:

1. An analytic device, comprising:
    a cassette having a fluidic element at least partially sealed with a deformable sealing layer;
    an actuator comprising an actuating plate adapted for rotational motion relative to the fluidic element, the actuating plate comprising at least one projection,
        the actuator further comprising at least one moveable body contained within a housing,
            the moveable body positioned between the plate and the cassette such that rotational motion of the actuating plate gives rise to the at least one projection contacting the moveable body so as to actuate the deformable sealing layer, the fluidic element, or both; and
    a motivator capable of controllably moving the actuating plate relative to the deformable sealing layer.

2. The analytic device of claim 1, wherein a fluidic element comprises a chamber, a channel, a valve, a mixer, a vent, a splitter, a switch, a reservoir, or any combination thereof.

3. The analytic device of claim 2, wherein the reservoir contains a buffer, an acid, a base, a growth medium, a dye, a label, a reagent, a biological material, a suspension, or any combination thereof.

4. The analytic device of claim 1, wherein the cassette comprises at least one vent to the exterior environment.

5. The analytic device of claim 1, wherein the plate comprises a disc.

6. The analytic device of claim 5, wherein a projection comprises a bump, a pyramid, a ramp, a wedge, or any combination thereof.

7. The analytic device of claim 1, wherein the projection is positioned such that movement of the actuating plate effects depression of the deformable sealing layer, actuation of a fluidic element, or both, in a predetermined sequence.

8. The analytic device of claim 1, wherein the motivator is capable of rotating the actuating plate.

9. The analytic device of claim 1, wherein the motivator comprises a timer.

10. The analytic device of claim 1, wherein the cassette comprises a removable film sealing a fluidic element.

11. The analytic device of claim 1, wherein the deformable sealing layer places two or more fluidic elements in fluidic communication with one another.

12. The analytic device of claim 1, wherein the actuator, the motivator, or both, are integrated into the cassette.

13. The analytic device of claim 2, wherein the fluidic element is contained within a substrate.

14. The analytic device of claim 13, wherein the substrate comprises a polymer, a glass, a metal, a ceramic, or any combination thereof.

15. The analytic device of claim 2, wherein a channel comprises a cross-sectional dimension in the range of from about 0.01 micrometers to about 5000 micrometers.

16. The analytic device of claim 2, wherein a fluidic element places the cassette into fluid communication with the environment exterior to the cassette.

17. The analytic device of claim 1, wherein the cassette further comprises a lateral flow strip, a microarray, a bead array, or any combination thereof.

18. The analytic device of claim 1, wherein the cassette defines a thickness of from about 0.5 millimeters to about 1 centimeter.

19. The analytic device of claim 1, wherein the cassette further comprises a sealing layer and a channeled connector layer, the channeled connector layer disposed so as to place a fluidic element of the cassette in fluid communication with another fluidic element of the cassette when the sealing layer is removed and the channeled connector layer is replaced.

* * * * *